(12) United States Patent
Lens et al.

(10) Patent No.: US 8,536,282 B2
(45) Date of Patent: Sep. 17, 2013

(54) SILYLATED POLYCARBONATE POLYMERS, METHOD OF MAKING, AND ARTICLES

(75) Inventors: Jan Pleun Lens, Breda (NL); Tilak Thulasi Raj, Bangalore (IN); Binod Behari Sahoo, Orissa (IN); Arakali Srinivasarao Radhakrishna, Bangalore (IN)

(73) Assignee: Momentive Performance Materials Inc., Waterford, NY (US)

( * ) Notice: Subject to any disclaimer, the term of this patent is extended or adjusted under 35 U.S.C. 154(b) by 0 days.

(21) Appl. No.: 12/555,155

(22) Filed: Sep. 8, 2009

(65) Prior Publication Data

US 2009/0326181 A1 Dec. 31, 2009

Related U.S. Application Data

(63) Continuation of application No. 11/962,754, filed on Dec. 21, 2007, now abandoned.

(60) Provisional application No. 60/871,657, filed on Dec. 22, 2006.

(51) Int. Cl.
| | |
|---|---|
| C08G 77/448 | (2006.01) |
| C07F 7/18 | (2006.01) |
| C08L 83/06 | (2006.01) |
| C08L 83/07 | (2006.01) |

(52) U.S. Cl.
USPC .............. 525/439; 525/464; 528/25; 528/29; 528/196; 528/204; 556/449

(58) Field of Classification Search
None
See application file for complete search history.

(56) References Cited

U.S. PATENT DOCUMENTS 7,678,864 B2 * 3/2010 Lens et al. ................. 525/439

FOREIGN PATENT DOCUMENTS

| JP | 2001-100 441 | 4/2001 |
| JP | 2002-214 807 | 7/2002 |
| JP | 2006344589 | * 12/2006 |
| WO | WO 2007080052 | * 7/2007 |

OTHER PUBLICATIONS

Grant & Hackh's Chemical Dictionary (5th Ed. 1987) at p. 148.*

* cited by examiner

*Primary Examiner* — Michael Barker
(74) *Attorney, Agent, or Firm* — Dominick G. Vicari; Joseph S. Ostroff

(57) ABSTRACT

A polycarbonate polymer or copolymer comprising pendant silylated dihydroxy aromatic compound of the formula (1a);

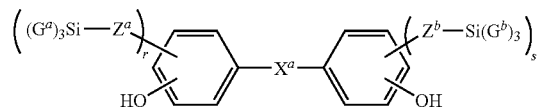

(1a)

wherein $G^a$ and $G^b$ are each independently $C_{1-12}$ alkyl, —OSi$(C_{1-12}$ alkyl$)_3$, $C_{1-12}$ arylalkyl, or —OSi$(C_{1-12}$ arylalkyl$)_3$; $Z^a$ and $Z^b$ are each independently a straight or branched $C_{2-18}$ is alkylene, a $C_{8-18}$ arylalkylene, or a $C_{8-18}$ alkylarylene, $X^a$ is a direct bond, a heteroatom-containing group, or a $C_{1-18}$ organic group, and r and s are each independently 1 or 2 is disclosed.

13 Claims, 1 Drawing Sheet

SILYLATED POLYCARBONATE POLYMERS, METHOD OF MAKING, AND ARTICLES

CROSS REFERENCE TO RELATED APPLICATIONS

This application is a continuation of U.S. application Ser. No. 11/962,754 filed Dec. 21, 2007, which claims priority to U.S. Provisional Application No. 60/871,657 filed Dec. 22, 2006.

BACKGROUND

This disclosure relates to polycarbonates, and in particular to silylated polycarbonates, methods of manufacture, and uses thereof.

Polycarbonates are useful in the manufacture of articles and components for a wide range of applications, from automotive parts to medical devices, because of their inherent properties of transparency, gloss, and impact strength. Polycarbonates can also be made to have improved resistance to photoyellowing. The combination of these properties make polycarbonates useful for exterior applications that require high resistance to environmental stresses such as impact, staining, resistance to scratching, such as for example automotive applications including door panels, bumpers, trim, or other such applications. However, polycarbonates generally present a more hydrophilic surface than other thermoplastics such as for example polyolefins, which can lead to more facile wetting of the surface of the polycarbonate and consequently a greater tendency to stain or to be affected by moisture-borne contaminants. In addition, polycarbonates generally do not have a high scratch resistance, and can therefore lose gloss and luster when subject to abrasive conditions.

There accordingly remains a need in the art for polycarbonates that have improved resistance to wetting. It would further be desirable for the polycarbonates to retain other advantageous properties, such as surface finish and impact strength, and/or transparency, while maintaining or improving abrasion resistance.

SUMMARY OF THE INVENTION

The above-described and other deficiencies of the art are met by a silylated polycarbonate comprising silylated carbonate units of the formula (1):

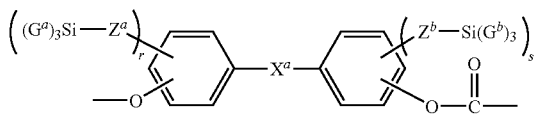

wherein $G^a$ and $G^b$ are each independently $C_{1-12}$ alkyl, —OSi$(C_{1-12}$ alkyl$)_3$, $C_{1-12}$ arylalkyl, or —OSi$(C_{1-12}$ arylalkyl$)_3$; $Z^a$ and $Z^b$ are each independently a straight or branched $C_{2-18}$ alkylene, a $C_{8-18}$ arylalkylene, or a $C_{8-18}$ alkylarylene, $X^a$ is a direct bond, a heteroatom-containing group, or a $C_{1-18}$ organic group, and r and s are each independently 1 or 2.

In another embodiment, a silylated polycarbonate comprises carbonate units derived from the silylated dihydroxyaromatic compound of the formula (1a):

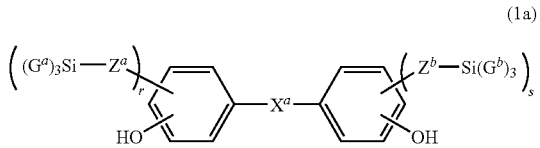

wherein $G^a$ and $G^b$ are each independently $C_{1-12}$ alkyl, —OSi$(C_{1-12}$ alkyl$)_3$, $C_{1-12}$ arylalkyl, or —OSi$(C_{1-12}$ arylalkyl$)_3$; $Z^a$ and $Z^b$ are each independently a straight or branched $C_{2-18}$ alkylene, a $C_{8-18}$ arylalkylene, or a $C_{8-18}$ alkylarylene, $X^a$ is a direct bond, a heteroatom-containing group, or a $C_{1-18}$ organic group, and r and s are each independently 1 or 2.

In another embodiment, a silylated dihydroxy aromatic compound has the formula (1a):

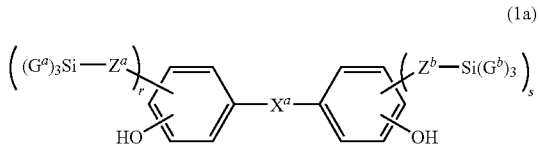

wherein $G^a$ and $G^b$ are each independently $C_{1-12}$ alkyl, —OSi$(C_{1-12}$ alkyl$)_3$, $C_{1-12}$ arylalkyl, or —OSi$(C_{1-12}$ arylalkyl$)_3$; $Z^a$ and $Z^b$ are each independently a straight or branched $C_{2-18}$ alkylene, a $C_{8-18}$ arylalkylene, or a $C_{8-18}$ alkylarylene, $X^a$ is a direct bond, a heteroatom containing group, or a $C_{1-18}$ organic group, and r and s are each independently 1 or 2.

In another embodiment, a silylated dihydroxy aromatic compound has the structure of formula (6):

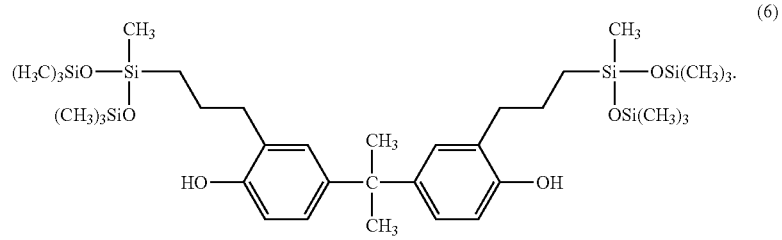

In another embodiment, a silylated dihydroxy aromatic compound has the structure of formula (7):

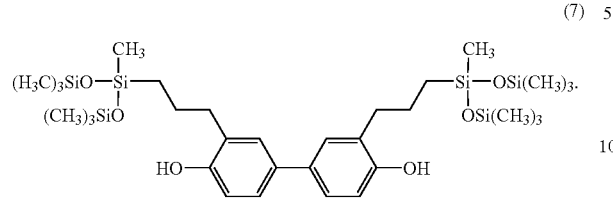
(7)

In another embodiment, a silylated polycarbonate comprises 1 to 100 mol % of carbonate units derived from a silylated isopropylidene bisphenol of the formula (5):

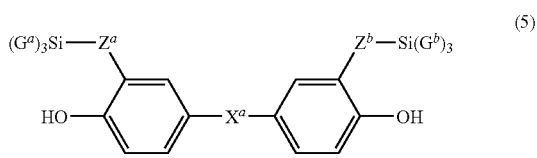
(5)

wherein $G^a$ and $G^b$ are each independently $C_{1-8}$ alkyl or —$OSi(C_{1-8}$ alkyl$)_3$; $Z^a$ and $Z^b$ are each independently a straight or branched $C_{2-8}$ alkylene, and $X^a$ is a direct bond or a $C_{1-12}$ alkylene group; and 0 to 99 mol % of carbonate units derived from a dihydroxy aromatic compound of formula (8):

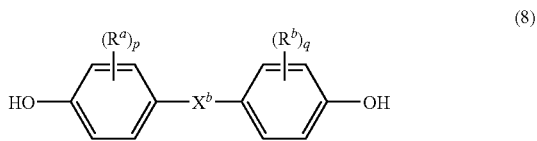
(8)

wherein $R^a$ and $R^b$ are each independently $C_{1-12}$ alkyl or halogen, p and q are each independently 0 or 1, and $X^b$ is:

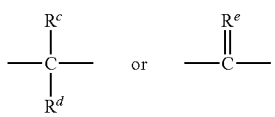

wherein $R^c$ and $R^d$ are each independently hydrogen, $C_{1-12}$ alkyl, cyclic $C_{1-12}$ alkyl, $C_{7-12}$ arylalkyl, $C_{1-12}$ heteroalkyl, or cyclic $C_{7-12}$ heteroarylalkyl, $R^e$ is a divalent $C_{1-12}$ hydrocarbon group, and the dihydroxy aromatic compound is not the same as the silylated dihydroxy aromatic compound; wherein each of the foregoing mole percents is based on the total moles of silylated dihydroxy aromatic compound and dihydroxy aromatic compound.

In an embodiment, a method of manufacture of the silylated polycarbonate, comprises interfacial polymerization of the silylated dihydroxy aromatic compound of formula (1a). In another embodiment, a method of manufacture of the silylated polycarbonate comprises melt polymerization of the silylated dihydroxy aromatic compound.

In another embodiment, a thermoplastic composition comprises a silylated polycarbonate, and an additive.

In another embodiment, an article comprises the silylated polycarbonate.

A description of the figures, which are meant to be exemplary and not limiting, is provided below.

Figure 1:
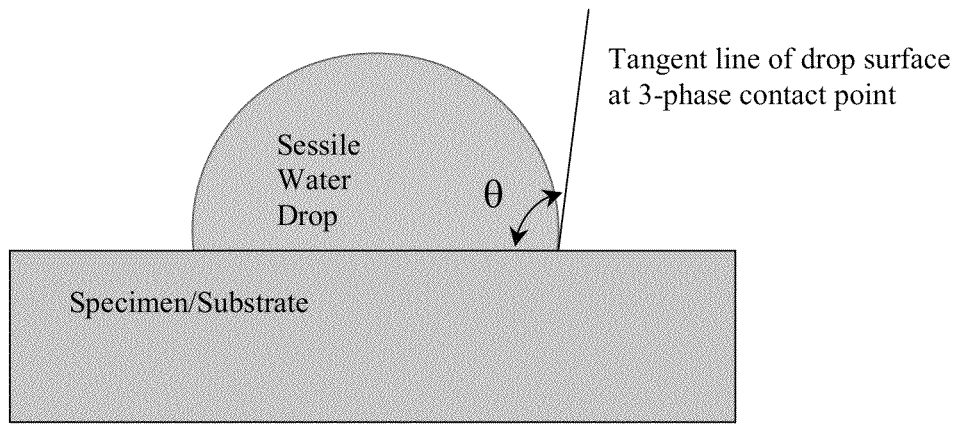
FIG. 1 is a diagram showing measurement of contact angle.

The above described and other features are exemplified by the following detailed description.

DETAILED DESCRIPTION OF THE INVENTION

Described herein is a novel silylated dihydroxy aromatic compound that is useful for preparing a polycarbonate. Surprisingly, a polycarbonate prepared using the silylated dihydroxy aromatic compound can be formed into an article that exhibits increased surface contact angle and lower wettability when compared with a polycarbonate that does not include the silylated dihydroxy aromatic compound. These silylated polycarbonates can have other advantageous properties as well, such as improved scratch resistance, impact strength, and transparency, and are particularly useful in high use exterior applications. The silylated dihydroxy aromatic compound can be polymerized to form the silylated polycarbonate under either phase-transfer polymerization conditions, or using melt polymerization conditions.

As used herein, the term "polycarbonate" includes generally homopolycarbonates and copolycarbonates have repeating structural carbonate units of the formula (2):

(2)

wherein the $R^1$ groups are derived from a dihydroxyaromatic compound.

Disclosed herein are silylated polycarbonates in which $R^1$ groups of carbonate units of formula (2) comprise silyl groups. Specifically, the silylated polycarbonate comprises silylated carbonate units shown in formula (1):

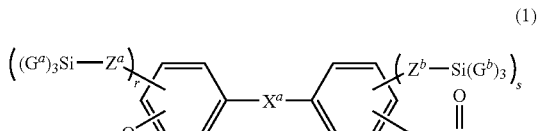
(1)

wherein $G^a$ and $G^b$ are each independently $C_{1-12}$ alkyl, —$OSi(C_{1-12}$ alkyl$)_3$, $C_{1-12}$ arylalkyl, or —$OSi(C_{1-12}$ arylalkyl$)_3$; $Z^a$ and $Z^b$ are each independently a straight or branched $C_{2-18}$ alkylene, a $C_{8-18}$ arylalkylene, or a $C_{8-18}$ alkylarylene, $X^a$ is a direct bond, a heteroatom-containing group, or a $C_{1-18}$ organic group, and r and s are each independently 1 or 2.

In an embodiment, the silylated carbonate unit of the silylated polycarbonates disclosed herein are polycarbonates in which the silylated carbonate units of formula (1) are derived from a dihydroxy aromatic compound comprising a silylated dihydroxyaromatic compound of the formula (1a):

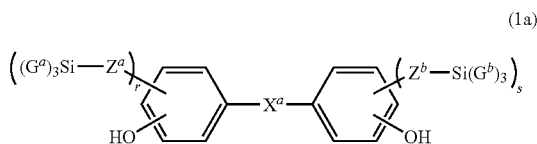

(1a)

wherein $G^a$, $G^b$, $Z^a$, $Z^b$, r, and s are each as described for formula (1), above. In an embodiment, $Z^a$ and $Z^b$ are each disposed ortho to a hydroxy group.

Also in formula (1a), $X^a$ represents a bridging group connecting the two hydroxy-substituted aromatic groups (i.e., hydroxy-substituted $C_6$ arylene groups such as, for example, phenol or o-cresol). In an embodiment, the bridging group and the hydroxy substituent of the $C_6$ arylene group are disposed para to each other on the $C_6$ arylene group. In an embodiment, the bridging group $X^a$ is a direct bond, a heteroatom-containing group such as S, S(O), S(O)$_2$, O, or a $C_{1-18}$ organic group. The $C_{1-18}$ organic bridging group can be cyclic or acyclic, aromatic or non-aromatic, substituted or unsubstituted, and can further comprise heteroatoms such as halogens, oxygen, nitrogen, sulfur, silicon, or phosphorous. The $C_{1-18}$ organic group can be disposed such that the $C_6$ arylene groups connected thereto are each connected to a common alkylidene carbon or to different carbons of the $C_{1-18}$ organic bridging group.

In an embodiment, $X^a$ is one of the groups of formula (3):

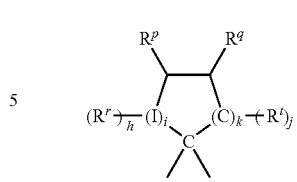

(3)

wherein $R^c$ and $R^d$ are each independently hydrogen, $C_{1-12}$ alkyl, cyclic $C_{1-12}$ alkyl, $C_{7-12}$ arylalkyl, $C_{1-12}$ heteroalkyl, or cyclic $C_{7-12}$ heteroarylalkyl, and $R^e$ is a divalent $C_{1-12}$ hydrocarbon group.

In another embodiment, $X^a$ is a $C_{1-18}$ alkylene group, a $C_{3-18}$ cycloalkylene group, a fused $C_{6-18}$ cycloalkylene group, or a group of the formula —B$^1$—W—B$^2$— wherein B$^1$ and B$^2$ are the same or different $C_{1-6}$ alkylene group and W is a $C_{3-12}$ cycloalkylene group or a $C_{6-16}$ arylene group.

In still another embodiment, $X^a$ is an acyclic $C_{1-18}$ alkylidene group, a $C_{4-18}$ cycloalkylidene group, or a $C_{2-18}$ heterocycloalkylidene group, i.e., a cycloalkylidene group having up to three heteroatoms in the ring, wherein the heteroatoms include —O—, —S—, or —N(Z)—, where Z is hydrogen, halogen, hydroxy, $C_{1-12}$ alkyl, $C_{1-12}$ alkoxy, or $C_{1-12}$ acyl.

$X^a$ can be a substituted $C_{4-18}$ cycloalkylidene of the formula (4):

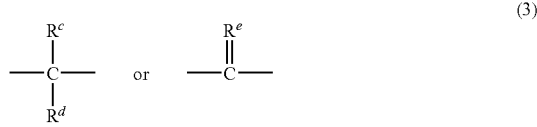

(4)

wherein each $R^r$, $R^p$, $R^q$, and $R^t$ is independently hydrogen, halogen, oxygen, or $C_{1-12}$ organic group; I is a direct bond, a carbon, or a divalent oxygen, sulfur, or —N(Z)— wherein Z is hydrogen, halogen, hydroxy, $C_{1-12}$ alkyl, $C_{1-12}$ alkoxy, or $C_{1-12}$ acyl; h is 0 to 2, j is 1 or 2, i is an integer of 0 or 1, and k is an integer of 0 to 3, with the proviso that at least two of $R^r$, $R^p$, $R^q$, and $R^t$ taken together are a fused cycloaliphatic, aromatic, or heteroaromatic ring. It will be understood that where the fused ring is aromatic, the ring as shown in formula (4) will have an unsaturated carbon-carbon linkage where the ring is fused. When k is one and i is 0, the ring as shown in formula (4) contains 4 carbon atoms, when k is 2, the ring as shown contains 5 carbon atoms, and when k is 3, the ring contains 6 carbon atoms. In one embodiment, two adjacent groups (e.g., $R^q$ and $R^t$ taken together) form an aromatic group, and in another embodiment, $R^q$ and $R^t$ taken together form one aromatic group and $R^r$ and $R^p$ taken together form a second aromatic group.

In an embodiment, in the silylated dihydroxy aromatic compound of formula (1a), $G^a$ and $G^b$ are each independently $C_{1-8}$ alkyl or —OSi($C_{1-8}$ alkyl)$_3$; $Z^a$ and $Z^b$ are each independently a straight or branched $C_{2-12}$ alkylene, r and s are each independently 1 to 2, $X^a$ is S, S(O), S(O)$_2$, O, a $C_{5-16}$ cycloalkylene, a $C_{5-16}$ cylcloalkylidene, a $C_{1-8}$ alkylene, a $C_{1-8}$ alkylidene, a $C_{6-13}$ arylene, a $C_{7-12}$ arylalkylene, $C_{7-12}$ arylalkylidene, a $C_{7-12}$ alkylarylene, or a $C_{7-12}$ arylenealkyl, and each of $Z^a$ and $Z^b$ is disposed ortho to the hydroxy group. It will be understood that, unless otherwise specified, hydrogen fills each carbon valency not occupied by a substituent group.

In a specific embodiment, the silylated dihydroxy aromatic compound has formula (5):

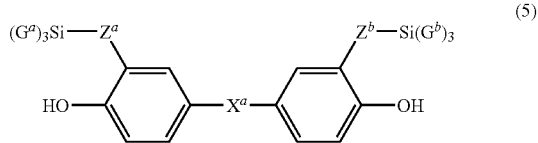

(5)

wherein $G^a$ and $G^b$ are each independently $C_{1-4}$ alkyl or —OSi($C_{1-4}$ alkyl)$_3$; $Z^a$ and $Z^b$ are each independently a straight or branched $C_{2-8}$ alkylene, and $X^a$ is a direct bond (—) or a $C_{1-12}$ alkylidene group. In a specific embodiment, $X^a$ is a direct bond or an isopropylidene group.

In an exemplary embodiment, the silylated dihydroxy aromatic compound comprises a silylated isopropylidene-bridged bisphenol of the formula (6):

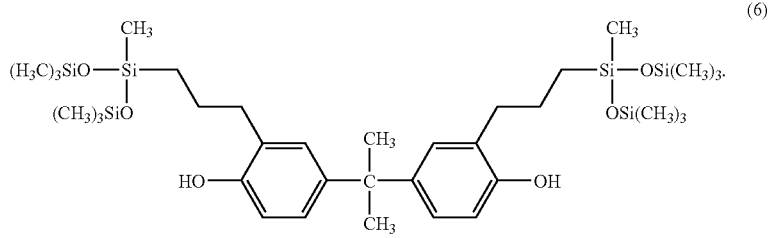

(6)

In another exemplary embodiment, the silylated dihydroxy aromatic compound comprises a silylated biphenol of the formula (7):

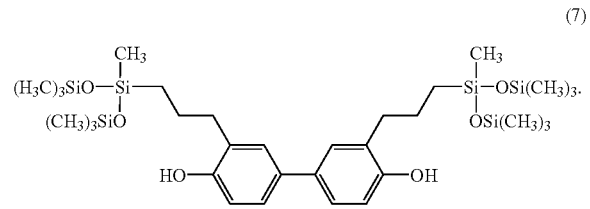

The polycarbonate, including the silylated polycarbonate as disclosed herein, can further comprise units derived from a bisphenol that differs from the silylated dihydroxy aromatic compound of formula (1a). The bisphenol is of the formula (8):

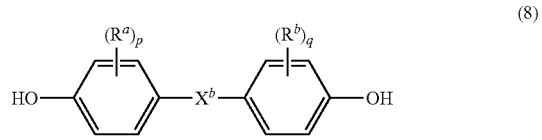

wherein $R^a$ and $R^b$ each represent halogen or $C_{1-12}$ alkyl and can be the same or different, and p and q are each independently integers of 0 to 4. It will be understood that when p and/or q is 0, the valency will be filled by a hydrogen atom. Also in formula (8), $X^b$ is as described for $X^a$, above.

Some illustrative, non-limiting examples of suitable bisphenol compounds include the following: 4,4'-dihydroxybiphenyl, 1,6-dihydroxynaphthalene, 2,6-dihydroxynaphthalene, bis(4-hydroxyphenyl)methane, bis(4-hydroxyphenyl)diphenylmethane, bis(4-hydroxyphenyl)-1-naphthylmethane, 1,2-bis(4-hydroxyphenyl)ethane, 1,1-bis(4-hydroxyphenyl)-1-phenylethane, 2-(4-hydroxyphenyl)-2-(3-hydroxyphenyl)propane, bis(4-hydroxyphenyl)phenylmethane, 2,2-bis(4-hydroxy-3-bromophenyl)propane, 1,1-bis(hydroxyphenyl)cyclopentane, 1,1-bis(4-hydroxyphenyl)cyclohexane, 1,1-bis(4-hydroxy-3 methyl phenyl)cyclohexane 1,1-bis(4-hydroxyphenyl)isobutene, 1,1-bis(4-hydroxyphenyl)cyclododecane, trans-2,3-bis(4-hydroxyphenyl)-2-butene, 2,2-bis(4-hydroxyphenyl)adamantine, (alpha,alpha'-bis(4-hydroxyphenyl)toluene, bis(4-hydroxyphenyl)acetonitrile, 2,2-bis(3-methyl-4-hydroxyphenyl)propane, 2,2-bis(3-ethyl-4-hydroxyphenyl)propane, 2,2-bis(3-n-propyl-4-hydroxyphenyl)propane, 2,2-bis(3-isopropyl-4-hydroxyphenyl)propane, 2,2-bis(3-sec-butyl-4-hydroxyphenyl)propane, 2,2-bis(3-t-butyl-4-hydroxyphenyl)propane, 2,2-bis(3-cyclohexyl-4-hydroxyphenyl)propane, 2,2-bis(3-allyl-4-hydroxyphenyl)propane, 2,2-bis(3-methoxy-4-hydroxyphenyl)propane, 2,2-bis(4-hydroxyphenyl)hexafluoropropane, 1,1-dichloro-2,2-bis(4-hydroxyphenyl)ethylene, 1,1-dibromo-2,2-bis(4-hydroxyphenyl)ethylene, 1,1-dichloro-2,2-bis(5-phenoxy-4-hydroxyphenyl)ethylene, 4,4'-dihydroxybenzophenone, 3,3-bis(4-hydroxyphenyl)-2-butanone, 1,6-bis(4-hydroxyphenyl)-1,6-hexanedione, ethylene glycol bis(4-hydroxyphenyl)ether, bis(4-hydroxyphenyl)ether, bis(4-hydroxyphenyl)sulfide, bis(4-hydroxyphenyl)sulfoxide, bis(4-hydroxyphenyl)sulfone, 9,9-bis(4-hydroxyphenyl)fluorene, 2,7-dihydroxypyrene, 6,6'-dihydroxy-3,3,3',3'-tetramethylspiro(bis)indane ("spirobiindane bisphenol"), 3,3-bis(4-hydroxyphenyl)phthalide, 2,6-dihydroxydibenzo-p-dioxin, 2,6-dihydroxythianthrene, 2,7-dihydroxyphenoxathin, 2,7-dihydroxy-9,10-dimethylphenazine, 3,6-dihydroxydibenzofuran, 3,6-dihydroxydibenzothiophene, and 2,7-dihydroxycarbazole, and the like, as well as combinations comprising at least one of the foregoing dihydroxy aromatic compounds.

Specific examples of the types of bisphenol compounds represented by formula (2) include 1,1-bis(4-hydroxyphenyl)methane, 1,1-bis(4-hydroxyphenyl)ethane, 2,2-bis(4-hydroxyphenyl)propane (hereinafter "bisphenol A" or "BPA"), 2,2-bis(4-hydroxyphenyl)butane, 2,2-bis(4-hydroxyphenyl)octane, 1,1-bis(4-hydroxyphenyl)propane, 1,1-bis(4-hydroxyphenyl)n-butane, 2,2-bis(4-hydroxy-1-methylphenyl)propane, 1,1-bis(4-hydroxy-t-butylphenyl)propane, 3,3-bis(4-hydroxyphenyl)phthalimidine, 2-phenyl-3,3-bis(4-hydroxyphenyl)phthalimidine ("PPPBP"), and 9,9-bis(4-hydroxyphenyl)fluorene. Combinations comprising at least one of the foregoing dihydroxy aromatic compounds can also be used.

Small amounts of other types of diols can be present in the silylated polycarbonate. For example, a small portion of $R^1$ can be derived from a dihydroxy aromatic compound of formula (9):

wherein each $R^f$ is independently $C_{1-12}$ alkyl, or halogen, and u is 0 to 4. It will be understood that $R^f$ is hydrogen when u is 0. Typically, the halogen can be chlorine or bromine. In an embodiment, compounds of formula (9) in which the —OH groups are substituted meta to one another, and wherein $R^f$ and u are as described above, are also generally referred to herein as resorcinols. Examples of compounds that can be represented by the formula (9) include resorcinol (where u is 0), substituted resorcinol compounds such as 5-methyl resorcinol, 5-ethyl resorcinol, 5-propyl resorcinol, 5-butyl resorcinol, 5-t-butyl resorcinol, 5-phenyl resorcinol, 5-cumyl resorcinol, 2,4,5,6-tetrafluoro resorcinol, 2,4,5,6-tetrabromo resorcinol, or the like; catechol; hydroquinone; substituted hydroquinones such as 2-methyl hydroquinone, 2-ethyl hydroquinone, 2-propyl hydroquinone, 2-butyl hydroquinone, 2-t-butyl hydroquinone, 2-phenyl hydroquinone, 2-cumyl hydroquinone, 2,3,5,6-tetramethyl hydroquinone, 2,3,5,6-tetra-t-butyl hydroquinone, 2,3,5,6-tetrafluoro hydroquinone, 2,3,5,6-tetrabromo hydroquinone, or the like; or combinations comprising at least one of the foregoing compounds.

Various types of polycarbonates with branching groups are also contemplated as being useful, provided that such branching does not significantly adversely affect desired properties of the polycarbonate. Branched polycarbonate blocks can be prepared by adding a branching agent during polymerization. These branching agents include polyfunctional organic compounds containing at least three functional groups selected from hydroxyl, carboxyl, carboxylic anhydride, haloformyl, and mixtures of the foregoing functional groups. Specific examples include trimellitic acid, trimellitic anhydride, trimellitic trichloride, tris-p-hydroxy phenyl ethane, isatin-bis-phenol, tris-phenol TC (1,3,5-tris((p-hydroxyphenyl)isopropyl)benzene), tris-phenol PA (4(4(1,1-bis(p-hydroxyphenyl)-ethyl)alpha,alpha-dimethyl benzyl)phenol), 4-chloroformyl phthalic anhydride, trimesic acid, and benzophenone tetracarboxylic acid. The branching agents can be added at a level of about 0.05 to about 2.0 wt %. Mixtures comprising linear polycarbonates and branched polycarbonates can be used.

The relative amount of each type of carbonate unit present in the silylated polycarbonate will depend on the desired properties of the copolymer, and are readily ascertainable by one of ordinary skill in the art without undue experimentation, using the guidance provided herein. In general, the silylated polycarbonate will comprise 1 to 100 mol %, specifically 10 to 100 mol %, even more specifically 15 to 100 mol % of silylated carbonate units of formula (1). In an embodiment, the silylated carbonate units are derived from the silylated dihydroxy aromatic compound of formula (1a). The silylated polycarbonate will further comprise 0 to 99 mol %, specifically 0 to 90 mol %, even more specifically 0 to 85 mol % of additional carbonate units. In an embodiment, each of the additional carbonate units is derived from the dihydroxy aromatic compound of formula (8). In a specific embodiment, the silylated polycarbonate is a homopolymer consisting essentially of carbonate units derived from the silylated dihydroxy aromatic compound of formula (1a). In another specific embodiment, the silylated polycarbonate is a copolymer comprising 1 to 60 mol %, specifically 5 to 50 mol %, more specifically 10 to 40 mol %, and still more specifically 10 to 30 mol % of silylated carbonate units of formula (1). In an embodiment, the silylated carbonate units are derived from silylated dihydroxyaromatic compound of formula (1a). Each of the foregoing mole percents is based on the total moles of silylated carbonate units of formula (1) and additional carbonate units. In an embodiment, where the silylated polycarbonate is derived from a silylated dihydroxy compound of formula (1a) and a dihydroxy aromatic compound of formula (8), the mole percents are based on the total moles of silylated dihydroxy compound of formula (1) and dihydroxy aromatic compound of formula (8) used to manufacture the silylated polycarbonate.

Other types of dihydroxy monomers, e.g., those of formula (9), can be used in amounts of up to 10 mol %, specifically up to 7 mol %, and even more specifically, up to 5 mol %. In an embodiment, the silylated polycarbonate consists essentially of units derived from the silylated dihydroxy aromatic compound and a dihydroxy compound, wherein any dihydroxy compounds used do not significantly adversely affect the desired properties of the silylated polycarbonate. In another embodiment, only monomers that fall within the scope of formulas (1a) and (8) are used, that is, the silylated polycarbonate consists of units derived from the silylated dihydroxy aromatic compound and dihydroxy aromatic compounds.

Also as disclosed herein, polycarbonates including the silylated polycarbonate can further include copolymers comprising carbonate units and other types of polymer units, such as ester units, polysiloxane units, and combinations comprising at least one of homopolycarbonates and copolycarbonates. A specific type of polycarbonate copolymer of this type is a polyester carbonate, also known as a polyester-polycarbonate. Such copolymers further contain, in addition to recurring carbonate chain units of the formula (2), carbonate units derived from oligomeric ester-containing dihydroxy compounds (also referred to herein as hydroxy end-capped oligomeric arylate esters) comprising repeating units of formula (10):

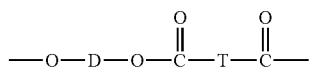

wherein D is a divalent group derived from a dihydroxy compound, and may be, for example, a $C_{2-10}$ alkylene group, a $C_{6-20}$ alicyclic group, a $C_{6-20}$ aromatic group or a polyoxyalkylene group in which the alkylene groups contain 2 to about 6 carbon atoms, specifically 2, 3, or 4 carbon atoms; and T divalent group derived from a dicarboxylic acid, and may be, for example, a $C_{2-10}$ alkylene group, a $C_{6-20}$ alicyclic group, a $C_{6-20}$ alkyl aromatic group, or a $C_{6-20}$ aromatic group.

In an embodiment, D is a $C_{2-30}$ alkylene group having a straight chain, branched chain, or cyclic (including polycyclic) structure. In another embodiment, D is derived from an aromatic dihydroxy aromatic compound of formula (8) above. In another embodiment, D is derived from a dihydroxy aromatic compound of formula (9) above.

Examples of aromatic dicarboxylic acids that may be used to prepare the polyester units include isophthalic or terephthalic acid, 1,2-di(p-carboxyphenyl)ethane, 4,4'-dicarboxydiphenyl ether, 4,4'-bisbenzoic acid, and combinations comprising at least one of the foregoing acids. Acids containing fused rings can also be present, such as in 1,4-, 1,5-, or 2,6-naphthalenedicarboxylic acids. Specific dicarboxylic acids are terephthalic acid, isophthalic acid, naphthalene dicarboxylic acid, cyclohexane dicarboxylic acid, or combinations thereof. A specific dicarboxylic acid comprises a combination of isophthalic acid and terephthalic acid wherein the weight ratio of isophthalic acid to terephthalic acid is about 91:9 to about 2:98. In another specific embodiment, D is a $C_{2-6}$ alkylene group and T is p-phenylene, m-phenylene, naphthalene, a divalent cycloaliphatic group, or a combination thereof. This class of polyester includes the poly(alkylene terephthalates).

The number of ester units in a polyester-polycarbonate is typically greater than or equal to 4, specifically greater than or equal to 5, and more specifically greater than or equal to 8. Also in an embodiment, the number of ester units of formula (10) is less than or equal to 100, specifically less than or equal to 90, more specifically less than or equal to 70. It will be understood that the low and high endpoint values for the number of ester units of formula (10) present are independently combinable. In a specific embodiment, the number of ester units of formula (10) in a polyester-polycarbonate can be 4 to 50, specifically 5 to 30, more specifically 8 to 25, and still more specifically 10 to 20. The molar ratio of ester units to carbonate units in the polyester-polycarbonate copolymers may vary broadly, for example 1:99 to 99:1, specifically 10:90 to 90:10, more specifically 25:75 to 75:25, depending on the desired properties of the final composition.

In a specific embodiment, the polyester unit of a polyester-polycarbonate may be derived from the reaction of a combination of isophthalic and terephthalic diacids (or derivatives thereof) with resorcinol. In another specific embodiment, the polyester unit of a polyester-polycarbonate is derived from the reaction of a combination of isophthalic acid and terephthalic acid with bisphenol-A. In a specific embodiment, the carbonate units of a polyester-polycarbonate can be derived from silylated dihydroxy aromatic compounds of formula (1a). Alternatively or in addition, in an exemplary embodiment, the carbonate units can be derived from resorcinol and/or bisphenol A. In another exemplary embodiment, the carbonate units of the polyester-polycarbonate can be derived from resorcinol and bisphenol A in a resulting molar ratio of resorcinol carbonate units to bisphenol A carbonate unit of 1:99 to 99:1.

Polycarbonates, including the silylated polycarbonates as disclosed herein can also be polysiloxane-polycarbonates comprising carbonate units of formula (2) and polysiloxane blocks derived from a siloxane-containing dihydroxy compounds (also referred to herein as "hydroxyaryl end-capped polysiloxanes") that contains diorganosiloxane units blocks of formula (11):

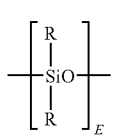

(11)

wherein each occurrence of R is same or different, and is a $C_{1-13}$ monovalent organic group. For example, R can be a $C_1$-$C_{13}$ alkyl group, $C_1$-$C_{13}$ alkoxy group, $C_2$-$C_{13}$ alkenyl group, $C_2$-$C_{13}$ alkenyloxy group, $C_3$-$C_6$ cycloalkyl group, $C_3$-$C_6$ cycloalkoxy group, $C_6$-$C_{14}$ aryl group, $C_6$-$C_{10}$ aryloxy group, $C_7$-$C_{13}$ aralkyl group, $C_7$-$C_{13}$ aralkoxy group, $C_7$-$C_{13}$ alkylaryl group, or $C_7$-$C_{13}$ alkylaryloxy group. The foregoing groups can be fully or partially halogenated with fluorine, chlorine, bromine, or iodine, or a combination thereof. In an embodiment, where a transparent silylated polycarbonate is desired, R does not contain any halogen. Combinations of the foregoing R groups can be used in the same silylated polycarbonate.

The value of E in formula (11) can vary widely depending on the type and relative amount of each of the different units in the silylated polycarbonate, the desired properties of the silylated polycarbonate, and like considerations. Generally, E can have an average value of about 2 to about 1,000, specifically about 2 to about 500, more specifically about 2 to about 100. In an embodiment, E has an average value of about 4 to about 90, specifically about 5 to about 80, and more specifically about 10 to about 70. Where E is of a lower value, e.g., less than about 40, it can be desirable to use a relatively larger amount of the units containing the polysiloxane. Conversely, where E is of a higher value, e.g., greater than about 40, it can be desirable to use a relatively lower amount of the units containing the polysiloxane.

In one embodiment, the polysiloxane blocks are provided by repeating structural units of formula (12):

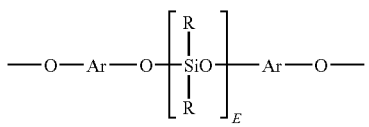

(12)

wherein E is as defined above; each R is the same or different, and is as defined above; and each Ar is the same or different, and is a substituted or unsubstituted $C_6$-$C_{30}$ arylene group, wherein the bonds are directly connected to an aromatic moiety. Ar groups in formula (12) can be derived from a $C_6$-$C_{30}$ dihydroxyarylene compound, for example a dihydroxyarylene compound of formula (8) or (9) described in detail below. Combinations comprising at least one of the foregoing dihydroxyarylene compounds can also be used. Exemplary dihydroxyarylene compounds are 1,1-bis(4-hydroxyphenyl)methane, 11-bis(4-hydroxyphenyl)ethane, 2,2-bis(4-hydroxyphenyl)propane, 2,2-bis(4-hydroxyphenyl)butane, 2,2-bis(4-hydroxyphenyl)octane, 11-bis(4-hydroxyphenyl)propane, 11-bis(4-hydroxyphenyl)n-butane, 2,2-bis(4-hydroxy-1-methylphenyl)propane, 11-bis(4-hydroxyphenyl)cyclohexane, bis(4-hydroxyphenyl sulfide), 11-bis(4-hydroxy-3-methylphenyl)cyclohexane, and 1,1-bis(4-hydroxy-t-butylphenyl)propane, or a combination comprising at least one of the foregoing dihydroxy compounds.

Polycarbonates comprising such units can be derived from the corresponding dihydroxy compound of formula (12a):

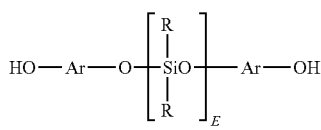

(12a)

wherein Ar and E are as described above. Compounds of formula (12a) can be obtained by the reaction of a dihydroxyarylene compound with, for example, an alpha, omega-bis-acetoxy-polydiorganosiloxane oligomer under phase transfer conditions. Compounds of formula (12a) can also be obtained from the condensation product of a dihydroxyarylene compound, with, for example, an alpha, omega bis-chloro-polydimethylsiloxane oligomer in the presence of an acid scavenger.

In another embodiment, polydiorganosiloxane blocks comprises units of formula (13):

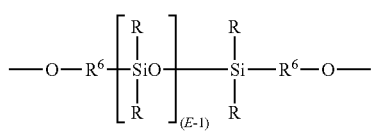

(13)

wherein R and E are as described above, and each $R^6$ is independently a divalent $C_1$-$C_{30}$ organic group, and wherein the oligomerized polysiloxane unit is the reaction residue of its corresponding dihydroxy compound. The polysiloxane blocks corresponding to formula (13) are derived from the corresponding dihydroxy compound (13a):

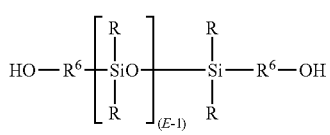

(13a)

wherein R and E and $R^6$ are as described for formula (13).

In a specific embodiment, the polydiorganosiloxane blocks are provided by repeating structural units of formula (14):

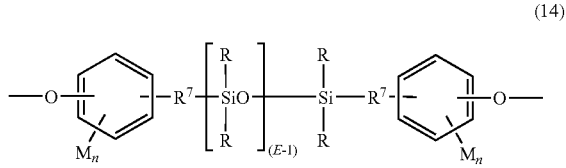

(14)

wherein R and E are as defined above. $R^7$ in formula (14) is a divalent $C_2$-$C_8$ aliphatic group. Each M in formula (14) can be the same or different, and is a halogen, cyano, nitro, $C_1$-$C_8$ alkylthio, $C_1$-$C_8$ alkyl, $C_1$-$C_8$ alkoxy, $C_2$-$C_8$ alkenyl, $C_2$-$C_8$ alkenyloxy group, $C_3$-$C_8$ cycloalkyl, $C_3$-$C_8$ cycloalkoxy, $C_6$-$C_{10}$ aryl, $C_6$-$C_{10}$ aryloxy, $C_7$-$C_{12}$ aralkyl, $C_7$-$C_{12}$ aralkoxy, $C_7$-$C_{12}$ alkylaryl, or $C_7$-$C_{12}$ alkylaryloxy, wherein each n is independently 0, 1, 2, 3, or 4.

In one embodiment, M is bromo or chloro, an alkyl group such as methyl, ethyl, or propyl, an alkoxy group such as methoxy, ethoxy, or propoxy, or an aryl group such as phenyl, chlorophenyl, or tolyl; $R^7$ is a dimethylene, trimethylene or tetramethylene group; and R is a $C_{1-8}$ alkyl, haloalkyl such as trifluoropropyl, cyanoalkyl, or aryl such as phenyl, chlorophenyl or tolyl. In another embodiment, R is methyl, or a combination of methyl and trifluoropropyl, or a combination of methyl and phenyl. In still another embodiment, M is methoxy, n is one, $R^7$ is a divalent $C_1$-$C_3$ aliphatic group, and R is methyl.

Polysiloxane-polycarbonates comprising units of formula (14) can be derived from the corresponding dihydroxy polydiorganosiloxane (14a):

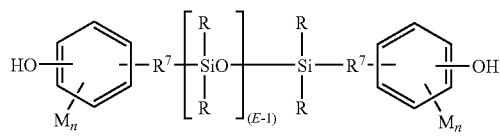

(14a)

wherein each of R, E, M, $R^7$, and n are as described above. Such dihydroxy polysiloxanes can be made by effecting a platinum-catalyzed addition between a siloxane hydride of formula (15):

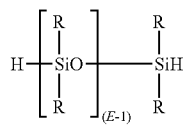

(15)

wherein R and E are as previously defined, and an aliphatically unsaturated monohydric phenol. Exemplary aliphatically unsaturated monohydric phenols included, for example, eugenol, 2-allylphenol, 4-allyl-2-methylphenol, 4-allyl-2-phenylphenol, 4-allyl-2-bromophenol, 4-allyl-2-t-butoxyphenol, 4-phenyl-2-phenylphenol, 2-methyl-4-propylphenol, 2-allyl-4,6-dimethylphenol, 2-allyl-4-bromo-6-methylphenol, 2-allyl-6-methoxy-4-methylphenol, 4-allylphenol, and 2-allyl-4,6-dimethylphenol. Combinations comprising at least one of the foregoing can also be used.

In an embodiment, the polysiloxane-polycarbonate can comprise polysiloxane blocks derived from the corresponding dihydroxy polysiloxane compound, present in an amount of 0.15 to 30 wt %, specifically 0.5 to 25 wt %, and more specifically 1 to 20 wt % based on the total weight of polysiloxane blocks and carbonate units. In a specific embodiment, the polysiloxane blocks are present in an amount of 1 to 10 wt %, specifically 2 to 9 wt %, and more specifically 3 to 8 wt %, based on the total weight of polysiloxane blocks and carbonate units.

Polysiloxane-polycarbonates further comprise carbonate units of formula (2) derived from a dihydroxy aromatic compound of formula (8). In an exemplary embodiment, the dihydroxy aromatic compound is bisphenol A. In an embodiment, the carbonate units comprising the polysiloxane-polycarbonate are present in an amount of 70 to 99.85 wt %, specifically 75 to 99.5, and more specifically 80 to 99 wt % based on the total weight of polysiloxane blocks and carbonate units. In a specific embodiment, the carbonate units are present in an amount of 90 to 99 wt %, specifically 91 to 98 wt %, and more specifically 92 to 97 wt %, based on the total weight of polysiloxane blocks and carbonate units.

The silylated polycarbonate comprises siloxane groups (where the siloxane is as derived from the hydridosiloxane precursor to the silylated dihydroxy aromatic compound of formula (1a)) in an amount of 0.5 to 57 wt %, specifically 1 to 57 wt %, even more specifically 2 to 57 wt % based on the total weight of the silylated polycarbonate. In a specific embodiment, the silylated polycarbonate comprises siloxane in an amount of 0.5 to 35 wt %, specifically 1 to 30 wt %, more specifically 2 to 25 wt %, and still more specifically 5 to 20 wt % based on the total weight of the silylated polycarbonate.

The silylated polycarbonates can have a weight average molecular weight of about 1,000 to about 100,000 g/mol, specifically about 5,000 to about 75,000 g/mol, and more specifically about 7,500 to about 50,000 g/mol as measured by gel permeation chromatography (GPC), using a crosslinked styrene-divinylbenzene column and calibrated to polycarbonate references. GPC samples are prepared in a solvent such as methylene chloride or chloroform at a concentration of about 1 mg/ml, and are eluted at a flow rate of about 1.5 ml/min.

Polycarbonates can have a melt volume ratio (MVR) of about 0.5 to about 80, more specifically about 2 to about 40 $cm^3$/10 minutes, measured at 300° C. under a load of 1.2 kg according to ASTM D1238-04.

The silylated polycarbonates can further be manufactured to be substantially transparent. In this case, the polycarbonate compositions can have a transparency of 0.5 to 10%, as measured using 3.2 mm plaques according to ASTM-D1003-00. Alternatively, or in addition, the silylated polycarbonates can have a haze of 0.5 to 5% as measured using 3.2 mm thick plaques according to ASTM-D1003-00.

Polycarbonates can be manufactured using an interfacial phase transfer process or melt polymerization. Although the reaction conditions for interfacial polymerization can vary, an exemplary process generally involves dissolving or dispersing a dihydric phenol reactant in aqueous caustic soda or potash, adding the resulting mixture to a water-immiscible solvent medium, and contacting the reactants with a carbonate precursor in the presence of a catalyst such as, for example, triethylamine or a phase transfer catalyst salt, under controlled pH conditions, e.g., about 8 to about 10.

Accordingly, the above-described hydroxy-containing monomers and an end-capping agent (e.g., a monophenol) in a biphasic solution are treated with sufficient caustic to achieve a pH of 8.0 to 9.0, then reacted with a carbonyl precursor (e.g., phosgene) in the presence of sufficient caustic to maintain a pH of 6.0 to 9.0, specifically 8.0 to 9.0, generally in the presence of a phase transfer catalyst.

Phase transfer catalysts include compounds of the formula $(R^3)_4Q^+X$, wherein each $R^3$ is the same or different, and is a $C_{1-10}$ alkyl group; Q is a nitrogen or phosphorus atom; and X is a halogen atom or a $C_{1-8}$ alkoxy group or $C_{6-18}$ aryloxy group. Exemplary phase transfer catalyst salts include, for example, $[CH_3(CH_2)_3]_4NX$, $[CH_3(CH_2)_3]_4PX$, $[CH_3(CH_2)_5]_4NX$, $[CH_3(CH_2)_6]_4NX$, $[CH_3(CH_2)_4]_4NX$, $CH_3$

[CH$_3$(CH$_2$)$_3$]$_3$NX, and CH$_3$[CH$_3$(CH$_2$)$_2$]$_3$NX, wherein X is C$^-$, Br$^-$, a C$_{1-8}$ alkoxy group or a C$_{6-18}$ aryloxy group.

Exemplary carbonate precursors include, for example, a carbonyl halide such as carbonyl bromide or carbonyl chloride, or a haloformate such as a bishaloformate of a dihydric phenol (e.g., the bischloroformates of bisphenol A, hydroquinone, or the like) or a glycol (e.g., the bishaloformate of ethylene glycol, neopentyl glycol, polyethylene glycol, or the like). Combinations comprising at least one of the foregoing types of carbonate precursors can also be used. Preferably, the process uses phosgene as a carbonate precursor.

The water-immiscible solvent used to provide a biphasic solution include, for example, methylene chloride, 1,2-dichloroethane, chlorobenzene, toluene, and the like.

The end-capping agent (also referred to as a chain stopper) limits molecular weight growth rate, and so controls molecular weight in the polycarbonate. Exemplary chain-stoppers include certain monophenolic compounds (i.e., phenyl compounds having a single free hydroxy group), monocarboxylic acid chlorides, and/or monochloroformates. Phenolic chain stoppers are exemplified by phenol and C$_1$-C$_{22}$ alkyl-substituted phenols such as p-cumyl-phenol, resorcinol monobenzoate, and p-tert-butyl phenol, cresol, and monoethers of diphenols, such as p-methoxyphenol. Alkyl-substituted phenols with branched chain alkyl substituents having 8 to 9 carbon atom can be specifically mentioned. Certain monophenolic UV absorbers can also be used as a capping agent, for example 4-substituted-2-hydroxybenzophenones and their derivatives, aryl salicylates, monoesters of diphenols such as resorcinol monobenzoate, 2-(2-hydroxyaryl)-benzotriazoles and their derivatives, 2-(2-hydroxyaryl)-1,3,5-triazines and their derivatives, and the like.

Suitable monocarboxylic acid chlorides include monocyclic, mono-carboxylic acid chlorides such as benzoyl chloride, C$_1$-C$_{22}$ alkyl-substituted benzoyl chloride, toluoyl chloride, halogen-substituted benzoyl chloride, bromobenzoyl chloride, cinnamoyl chloride, 4-nadimidobenzoyl chloride, and combinations thereof; polycyclic, mono-carboxylic acid chlorides such as trimellitic anhydride chloride, and naphthoyl chloride; and combinations of monocyclic and polycyclic mono-carboxylic acid chlorides. Chlorides of aliphatic monocarboxylic acids with less than or equal to about 22 carbon atoms are useful. Functionalized chlorides of aliphatic monocarboxylic acids, such as acryloyl chloride and methacryoyl chloride, are also useful. Also useful are monochloroformates including monocyclic monochloroformates, such as phenyl chloroformate, C$_1$-C$_{22}$ alkyl-substituted phenyl chloroformate, p-cumyl phenyl chloroformate, toluene chloroformate, and combinations thereof.

Alternatively, melt processes can be used to make the polycarbonates, including silylated polycarbonates. Generally, in the melt polymerization process, polycarbonates may be prepared by co-reacting, in a molten state, the dihydroxy reactant(s) and a diaryl carbonate ester, such as diphenyl carbonate, in the presence of a transesterification catalyst in a Banbury® mixer, single or twin screw extruder, or the like to form a uniform dispersion. Volatile monohydric phenol is removed from the molten reactants by distillation and the polymer is isolated as a molten residue. A specifically useful melt process for making polycarbonates uses a diaryl carbonate ester having electron-withdrawing substituents on the aryls. Examples of specifically useful diaryl carbonate esters with electron withdrawing substituents include bis(4-nitrophenyl)carbonate, bis(2-chlorophenyl)carbonate, bis(4-chlorophenyl)carbonate, bis(methyl salicyl)carbonate, bis(4-methylcarboxylphenyl)carbonate, bis(2-acetylphenyl) carboxylate, bis(4-acetylphenyl)carboxylate, or a combination comprising at least one of the foregoing. In addition, exemplary transesterification catalysts may include phase transfer catalysts of formula (R$^3$)$_4$Q$^+$X above, wherein each R$^3$, Q, and X are as defined above. Examples of such transesterification catalysts include tetrabutylammonium hydroxide, methyltributylammonium hydroxide, tetrabutylammonium acetate, tetrabutylphosphonium hydroxide, tetrabutylphosphonium acetate, tetrabutylphosphonium phenolate, or a combination comprising at least one of the foregoing.

It has been found that typical polycarbonates such as, e.g., bisphenol-A polycarbonate, can have surface properties that render them sufficiently hydrophilic such that the surface of an article prepared using the polycarbonate can attract and retain, and do not readily shed or dissipate, moisture (i.e., water). The hydrophilicity of a surface can be measured by the contact angle of a sessile drop of contaminant-free water placed on the surface, and measuring the tangential angle of contact between the drop and the surface. For polycarbonate, the contact angle is typically about 75° to 80°, indicating a relatively high wettability for a polymeric substrate. To the extent that contaminants carried in the moisture can be deposited on the surface of an article made from the polycarbonate upon evaporation of the moisture, surfaces with greater hydrophilicity (i.e., lower contact angle) can lead to greater retention of such contaminants, which can manifest as visually presenting a contaminated, e.g., dirty, surface. Such surfaces are less desirable where the appearance after the dissipation of the moisture should be visually free of contamination for aesthetic purposes, or for applications where a contaminant-free surface is otherwise desirable.

Disclosed herein a novel silylated dihydroxy aromatic compound of formula (1a) having pendant siloxane groups. Surprisingly, it has been found that a silylated polycarbonate prepared using the silylated dihydroxy aromatic compound can be formed into an article that exhibits significantly increased surface contact angle when compared with a polycarbonate that does not include the silylated dihydroxy aromatic compound. The surfaces of articles prepared from silylated polycarbonate as disclosed herein can have a surface contact angle of at least 95° or greater, and consequently can more effectively shed and disperse moisture than a polycarbonate prepared without the silylated dihydroxy aromatic compound. These copolymers can have other advantageous properties as well, such as improved scratch resistance and transparency. The silylated polycarbonates are therefore particularly useful in high use exterior applications that are exposed to wet environmental conditions.

The silylated polycarbonate can be combined with other components to provide a thermoplastic composition, where types and amounts of the other components are present such that the desired properties of the thermoplastic composition are not significantly adversely affected by these other components. In an embodiment, the thermoplastic composition consists essentially of the silylated polycarbonate.

The thermoplastic compositions prepared using the silylated polycarbonates desirably have, when measure using a sessile water droplet, a mean surface contact angle of greater than or equal to 97°, specifically greater than or equal to 98°, still more specifically greater than or equal to 99°, and still more specifically greater than or equal to 100°.

In addition to the silylated polycarbonates described above, thermoplastic compositions comprising combinations of the silylated polycarbonate with other thermoplastic polymers that do not comprise the silylated carbonate units of formula (1) can be prepared using, for example homopolycarbonates, other polycarbonate copolymers (i.e., copolycarbonates) comprising different R¹ moieties in the carbonate units, polysiloxane-polycarbonates, polyester-carbonates (also referred to as a polyester-polycarbonates), and polyesters. These combinations can comprise 1 to 99 wt %, specifically 10 to 90, more specifically 20 to 80 wt % of the silylated polycarbonate, with the remainder of the compositions being other of the foregoing polymers, and/or additives as described below.

For example, the thermoplastic composition can further include as an additive an impact modifier(s). Suitable impact modifiers are typically high molecular weight elastomeric materials derived from olefins, monovinyl aromatic monomers, acrylic and methacrylic acids and their ester derivatives, as well as conjugated dienes. The polymers formed from conjugated dienes can be fully or partially hydrogenated. The elastomeric materials can be in the form of homopolymers or copolymers, including random, block, radial block, graft, and core-shell copolymers. Combinations of impact modifiers can be used.

A specific type of impact modifier is an elastomer-modified graft copolymer comprising an elastomeric (i.e., rubbery) polymer substrate having a Tg less than about 10° C., more specifically less than about −10° C., or more specifically about −40° to −80° C., and (ii) a rigid polymeric superstrate grafted to the elastomeric polymer substrate. Materials suitable for use as the elastomeric phase include, for example, conjugated diene rubbers, for example polybutadiene and polyisoprene; copolymers of a conjugated diene with less than about 50 wt % of a copolymerizable monomer, for example a monovinylic compound such as styrene, acrylonitrile, n-butyl acrylate, or ethyl acrylate; olefin rubbers such as ethylene propylene copolymers (EPR) or ethylene-propylene-diene monomer rubbers (EPDM); ethylene-vinyl acetate rubbers; silicone rubbers; elastomeric $C_{1-8}$ alkyl (meth)acrylates; elastomeric copolymers of $C_{1-8}$ alkyl (meth)acrylates with butadiene and/or styrene; or combinations comprising at least one of the foregoing elastomers materials suitable for use as the rigid phase include, for example, monovinyl aromatic monomers such as styrene and alpha-methyl styrene, and monovinylic monomers such as acrylonitrile, acrylic acid, methacrylic acid, and the $C_1$-$C_6$ esters of acrylic acid and methacrylic acid, specifically methyl methacrylate.

Specific exemplary elastomer-modified graft copolymers include those formed from styrene-butadiene-styrene (SBS), styrene-butadiene rubber (SBR), styrene-ethylene-butadiene-styrene (SEBS), ABS (acrylonitrile-butadiene-styrene), acrylonitrile-ethylene-propylene-diene-styrene (AES), styrene-isoprene-styrene (SIS), methyl methacrylate-butadiene-styrene (MBS), and styrene-acrylonitrile (SAN).

Impact modifiers are generally present in amounts of 1 to 30 wt %, based on the total weight of the polymers in the composition.

In addition to the silylated polycarbonate, the thermoplastic composition can include various additives ordinarily incorporated in resin compositions of this type, with the proviso that the additives are selected so as to not significantly adversely affect the desired properties of the thermoplastic composition. Combinations of additives can be used. Such additives can be mixed at a suitable time during the mixing of the components for forming the composition.

Possible fillers or reinforcing agents include, for example, silicates and silica powders such as aluminum silicate (mullite), synthetic calcium silicate, zirconium silicate, fused silica, crystalline silica graphite, natural silica sand, or the like; boron powders such as boron-nitride powder, boron-silicate powders, or the like; oxides such as $TiO_2$, aluminum oxide, magnesium oxide, or the like; calcium sulfate (as its anhydride, dihydrate or trihydrate); calcium carbonates such as chalk, limestone, marble, synthetic precipitated calcium carbonates, or the like; talc, including fibrous, modular, needle shaped, lamellar talc, or the like; wollastonite; surface-treated wollastonite; glass spheres such as hollow and solid glass spheres, silicate spheres, cenospheres, aluminosilicate (armospheres), or the like; kaolin, including hard kaolin, soft kaolin, calcined kaolin, kaolin comprising various coatings known in the art to facilitate compatibility with the polymeric matrix resin, or the like; single crystal fibers or "whiskers" such as silicon carbide, alumina, boron carbide, iron, nickel, copper, or the like; fibers (including continuous and chopped fibers) such as asbestos, carbon fibers, glass fibers, such as E, A, C, ECR, R, S, D, or NE glasses, or the like; sulfides such as molybdenum sulfide, zinc sulfide or the like; barium compounds such as barium titanate, barium ferrite, barium sulfate, heavy spar, or the like; metals and metal oxides such as particulate or fibrous aluminum, bronze, zinc, copper and nickel or the like; flaked fillers such as glass flakes, flaked silicon carbide, aluminum diboride, aluminum flakes, steel flakes or the like; fibrous fillers, for example short inorganic fibers such as those derived from blends comprising at least one of aluminum silicates, aluminum oxides, magnesium oxides, and calcium sulfate hemihydrate or the like; natural fillers and reinforcements, such as wood flour obtained by pulverizing wood, fibrous products such as cellulose, cotton, sisal, jute, starch, cork flour, lignin, ground nut shells, corn, rice grain husks or the like; organic fillers such as polytetrafluoroethylene; reinforcing organic fibrous fillers formed from organic polymers capable of forming fibers such as poly(ether ketone), polyimide, polybenzoxazole, poly(phenylene sulfide), polyesters, polyethylene, aromatic polyamides, aromatic polyimides, polyetherimides, polytetrafluoroethylene, acrylic resins, poly(vinyl alcohol) or the like; as well as additional fillers and reinforcing agents such as mica, clay, feldspar, flue dust, fillite, quartz, quartzite, perlite, tripoli, diatomaceous earth, carbon black, or the like, or combinations comprising at least one of the foregoing fillers or reinforcing agents.

The fillers and reinforcing agents can be coated with a layer of metallic material to facilitate conductivity, or surface treated with silanes to improve adhesion and dispersion with the polymeric matrix resin. In addition, the reinforcing fillers can be provided in the form of monofilament or multifilament fibers and can be used individually or in combination with other types of fiber, through, for example, co-weaving or core/sheath, side-by-side, orange-type or matrix and fibril constructions, or by other methods known to one skilled in the art of fiber manufacture. Exemplary co-woven structures include, for example, glass fiber-carbon fiber, carbon fiber-aromatic polyimide (aramid) fiber, and aromatic polyimide fiberglass fiber or the like. Fibrous fillers can be supplied in the form of, for example, rovings, woven fibrous reinforcements, such as 0-90 degree fabrics or the like; non-woven fibrous reinforcements such as continuous strand mat, chopped strand mat, tissues, papers and felts or the like; or three-dimensional reinforcements such as braids. Fillers are generally used in amounts of about 1 to about 20 parts by weight, based on 100 parts by weight of silylated polycarbonate and impact modifier.

Exemplary antioxidant additives include, for example, organophosphites such as tris(nonyl phenyl)phosphite, tris(2,4-di-t-butylphenyl)phosphite, bis(2,4-di-t-butylphenyl)pentaerythritol diphosphite, distearyl pentaerythritol diphosphite or the like; alkylated monophenols or polyphenols; alkylated reaction products of polyphenols with dienes, such as tetrakis [methylene(3,5-di-tert-butyl-4-hydroxyhydrocinnamate)]

methane, or the like; butylated reaction products of para-cresol or dicyclopentadiene; alkylated hydroquinones; hydroxylated thiodiphenyl ethers; alkylidene-bisphenols; benzyl compounds; esters of beta-(3,5-di-tert-butyl-4-hydroxyphenyl)-propionic acid with monohydric or polyhydric alcohols; esters of beta-(5-tert-butyl-4-hydroxy-3-methylphenyl)-propionic acid with monohydric or polyhydric alcohols; esters of thioalkyl or thioaryl compounds such as distearylthiopropionate, dilaurylthiopropionate, ditridecylthiodipropionate, octadecyl-3-(3,5-di-tert-butyl-4-hydroxyphenyl)propionate, pentaerythrityl-tetrakis[3-(3,5-di-tert-butyl-4-hydroxyphenyl)propionate or the like; amides of beta-(3,5-di-tert-butyl-4-hydroxyphenyl)-propionic acid or the like, or combinations comprising at least one of the foregoing antioxidants. Antioxidants are generally used in amounts of about 0.01 to about 0.1 parts by weight, based on 100 parts by weight of silylated polycarbonate and impact modifier.

Exemplary heat stabilizer additives include, for example, organophosphites such as triphenyl phosphite, tris-(2,6-dimethylphenyl)phosphite, tris-(mixed mono- and di-nonylphenyl)phosphite or the like; phosphonates such as dimethylbenzene phosphonate or the like, phosphates such as trimethyl phosphate, or the like, or combinations comprising at least one of the foregoing heat stabilizers. Heat stabilizers are generally used in amounts of about 0.01 to about 0.1 parts by weight, based on 100 parts by weight of silylated polycarbonate and impact modifier.

Light stabilizers and/or ultraviolet light (UV) absorbing additives can also be used. Exemplary light stabilizer additives include, for example, benzotriazoles such as 2-(2-hydroxy-5-methylphenyl)benzotriazole, 2-(2-hydroxy-5-tert-octylphenyl)benzotriazole and 2-hydroxy-4-n-octoxy benzophenone, or the like, or combinations comprising at least one of the foregoing light stabilizers. Light stabilizers are generally used in amounts of about 0.01 to about 5 parts by weight, based on 100 parts by weight of silylated polycarbonate and impact modifier.

Exemplary UV absorbing additives include for example, hydroxybenzophenones; hydroxybenzotriazoles; hydroxybenzotriazines; cyanoacrylates; oxanilides; benzoxazinones; 2-(2H-benzotriazol-2-yl)-4-(1,1,3,3-tetramethylbutyl)-phenol (CYASORB® 5411); 2-hydroxy-4-n-octyloxybenzophenone (CYASORB® 531); 2-[4,6-bis(2,4-dimethylphenyl)-1,3,5-triazin-2-yl]-5-(octyloxy)-phenol (CYASORB® 1164); 2,2'-(1,4-phenylene)bis(4H-3,1-benzoxazin-4-one) (CYASORB® UV-3638); 1,3-bis[(2-cyano-3,3-diphenylacryloyl)oxy]-2,2-bis[[(2-cyano-3,3-diphenylacryloyl)oxy]methyl] propane (UVINUL® 3030); 2,2'-(1,4-phenylene)bis(4H-3,1-benzoxazin-4-one); 1,3-bis[(2-cyano-3,3-diphenylacryloyl)oxy]-2,2-bis[[(2-cyano-3,3-diphenylacryloyl)oxy]methyl] propane; nano-size inorganic materials such as titanium oxide, cerium oxide, and zinc oxide, all with particle size less than or equal to about 100 nanometers; or the like, or combinations comprising at least one of the foregoing UV absorbers. UV absorbers are generally used in amounts of about 0.01 to about 5 parts by weight, based on 100 parts by weight of silylated polycarbonate and impact modifier.

Plasticizers, lubricants, and/or mold release agents can also be used. There is considerable overlap among these types of materials, which include, for example, phthalic acid esters such as dioctyl-4,5-epoxy-hexahydrophthalate; tris-(octoxycarbonylethyl)isocyanurate; tristearin; di- or polyfunctional aromatic phosphates such as resorcinol tetraphenyl diphosphate (RDP), the bis(diphenyl)phosphate of hydroquinone and the bis(diphenyl)phosphate of bisphenol-A; poly-alpha-olefins; epoxidized soybean oil; silicones, including silicone oils; esters, for example, fatty acid esters such as alkyl stearyl esters, e.g., methyl stearate, stearyl stearate, pentaerythritol tetrastearate, and the like; combinations of methyl stearate and hydrophilic and hydrophobic nonionic surfactants comprising polyethylene glycol polymers, polypropylene glycol polymers, poly(ethylene glycol-co-propylene glycol) copolymers, or a combination comprising at least one of the foregoing glycol polymers, e.g., methyl stearate and polyethylene-polypropylene glycol copolymer in a suitable solvent; waxes such as beeswax, montan wax, paraffin wax, or the like. Such materials are generally used in amounts of about 0.1 to about 1 parts by weight, based on 100 parts by weight of silylated polycarbonate and impact modifier.

The term "antistatic agent" refers to monomeric, oligomeric, or polymeric materials that can be processed into polymer resins and/or sprayed onto materials or articles to improve conductive properties and overall physical performance. Examples of monomeric antistatic agents include glycerol monostearate, glycerol distearate, glycerol tristearate, ethoxylated amines, primary, secondary and tertiary amines, ethoxylated alcohols, alkyl sulfates, alkylarylsulfates, alkylphosphates, alkylaminesulfates, alkyl sulfonate salts such as sodium stearyl sulfonate, sodium dodecylbenzenesulfonate or the like, quaternary ammonium salts, quaternary ammonium resins, imidazoline derivatives, sorbitan esters, ethanolamides, betaines, or the like, or combinations comprising at least one of the foregoing monomeric antistatic agents.

Exemplary polymeric antistatic agents include certain polyesteramides polyether-polyamide (polyetheramide) block copolymers, polyetheresteramide block copolymers, polyetheresters, or polyurethanes, each containing polyalkylene glycol moieties polyalkylene oxide units such as polyethylene glycol, polypropylene glycol, polytetramethylene glycol, and the like. Such polymeric antistatic agents are commercially available, for example PELESTAT® 6321 (Sanyo) or PEBAX® MH1657 (Atofina), IRGASTAT® P18 and P22 (Ciba-Geigy). Other polymeric materials that can be used as antistatic agents are inherently conducting polymers such as polyaniline (commercially available as PANIPOL® EB from Panipol), polypyrrole and polythiophene (commercially available from Bayer), which retain some of their intrinsic conductivity after melt processing at elevated temperatures. In one embodiment, carbon fibers, carbon nanofibers, carbon nanotubes, carbon black, or a combination comprising at least one of the foregoing can be used in a polymeric resin containing chemical antistatic agents to render the composition electrostatically dissipative. Antistatic agents are generally used in amounts of about 0.05 to about 0.5 parts by weight, based on 100 parts by weight of silylated polycarbonate and impact modifier.

Colorants such as pigment and/or dye additives can also be present. Useful pigments can include, for example, inorganic pigments such as metal oxides and mixed metal oxides such as zinc oxide, titanium dioxides, iron oxides, or the like; sulfides such as zinc sulfides, or the like; aluminates; sodium sulfo-silicates sulfates, chromates, or the like; carbon blacks; zinc ferrites; ultramarine blue; organic pigments such as azos, di-azos, quinacridones, perylenes, naphthalene tetracarboxylic acids, flavanthrones, isoindolinones, tetrachloroisoindolinones, anthraquinones, enthrones, dioxazines, phthalocyanines, and azo lakes; Pigment Red 101, Pigment Red 122, Pigment Red 149, Pigment Red 177, Pigment Red 179, Pigment Red 202, Pigment Violet 29, Pigment Blue 15, Pigment Blue 60, Pigment Green 7, Pigment Yellow 119, Pigment Yellow 147, Pigment Yellow 150, and Pigment Brown 24; or combinations comprising at least one of the foregoing pigments. Pigments are generally used in amounts of about 0.001 to about 3 parts by weight, based on 100 parts by weight of silylated polycarbonate and impact modifier.

Exemplary dyes are generally organic materials and include, for example, coumarin dyes such as coumarin 460 (blue), coumarin 6 (green), nile red or the like; lanthanide complexes; hydrocarbon and substituted hydrocarbon dyes; polycyclic aromatic hydrocarbon dyes; scintillation dyes such as oxazole or oxadiazole dyes; aryl- or heteroaryl-substituted poly ($C_{2-8}$) olefin dyes; carbocyanine dyes; indanthrone dyes; phthalocyanine dyes; oxazine dyes; carbostyryl dyes; napthalenetetracarboxylic acid dyes; porphyrin dyes; bis(styryl)biphenyl dyes; acridine dyes; anthraquinone dyes; cyanine dyes; methine dyes; arylmethane dyes; azo dyes; indigoid dyes, thioindigoid dyes, diazonium dyes; nitro dyes; quinone imine dyes; aminoketone dyes; tetrazolium dyes; thiazole dyes; perylene dyes, perinone dyes; bis-benzoxazolylthiophene (BBOT); triarylmethane dyes; xanthene dyes; thioxanthene dyes; naphthalimide dyes; lactone dyes; fluorophores such as anti-stokes shift dyes which absorb in the near infrared wavelength and emit in the visible wavelength, or the like; luminescent dyes such as 7-amino-4-methylcoumarin; 3-(2'-benzothiazolyl)-7-diethylaminocoumarin; 2-(4-biphenylyl)-5-(4-t-butylphenyl)-1,3,4-oxadiazole; 2,5-bis-(4-biphenylyl)-oxazole; 2,2'-dimethyl-p-quaterphenyl; 2,2-dimethyl-p-terphenyl; 3,5,3"",5""-tetra-t-butyl-p-quinquephenyl; 2,5-diphenylfuran; 2,5-diphenyloxazole; 4,4'-diphenylstilbene; 4-dicyanomethylene-2-methyl-6-(p-dimethylaminostyryl)-4H-pyran; 1,1'-diethyl-2,2'-carbocyanine iodide; 3,3'-diethyl-4,4',5,5'-dibenzothiatricarbocyanine iodide; 7-dimethylamino-1-methyl-4-methoxy-8-azaquinolone-2; 7-dimethylamino-4-methylquinolone-2; 2-(4-(4-dimethylaminophenyl)-1,3-butadienyl)-3-ethylbenzothiazolium perchlorate; 3-diethylamino-7-diethyliminophenoxazonium perchlorate; 2-(1-naphthyl)-5-phenyloxazole; 2,2'-p-phenylen-bis(5-phenyloxazole); rhodamine 700; rhodamine 800; pyrene, chrysene, rubrene, coronene, or the like; or combinations comprising at least one of the foregoing dyes. Dyes are generally used in amounts of about 0.0001 to about 5 parts by weight, based on 100 parts by weight of silylated polycarbonate and impact modifier.

Where a foam is desired, useful blowing agents include for example, low boiling halohydrocarbons and those that generate carbon dioxide; blowing agents that are solid at room temperature and when heated to temperatures higher than their decomposition temperature, generate gases such as nitrogen, carbon dioxide, and ammonia gas, such as azodicarbonamide, metal salts of azodicarbonamide, 4,4'oxybis (benzenesulfonylhydrazide), sodium bicarbonate, ammonium carbonate, or the like, or combinations comprising at least one of the foregoing blowing agents. Blowing agents are generally used in amounts of about 1 to about 20 parts by weight, based on 100 parts by weight of silylated polycarbonate and impact modifier.

Useful flame retardants include organic compounds that include phosphorus, bromine, and/or chlorine. Non-brominated and non-chlorinated phosphorus-containing flame retardants can be preferred in certain applications for regulatory reasons, for example organic phosphates and organic compounds containing phosphorus-nitrogen bonds.

One type of exemplary organic phosphate is an aromatic phosphate of the formula $(GO)_3P=O$, wherein each G is independently an alkyl, cycloalkyl, aryl, alkylaryl, or aralkyl group, provided that at least one G is an aromatic group. Two of the G groups can be joined together to provide a cyclic group, for example, diphenyl pentaerythritol diphosphate. Exemplary aromatic phosphates include, phenyl bis(dodecyl) phosphate, phenyl bis(neopentyl)phosphate, phenyl bis(3,5,5'-trimethylhexyl)phosphate, ethyl diphenyl phosphate, 2-ethylhexyl di(p-tolyl)phosphate, bis(2-ethylhexyl)p-tolyl phosphate, tritolyl phosphate, bis(2-ethylhexyl)phenyl phosphate, tri(nonylphenyl)phosphate, bis(dodecyl) p-tolyl phosphate, dibutyl phenyl phosphate, 2-chloroethyl diphenyl phosphate, p-tolyl bis(2,5,5'-trimethylhexyl)phosphate, 2-ethylhexyl diphenyl phosphate, or the like. A specific aromatic phosphate is one in which each G is aromatic, for example, triphenyl phosphate, tricresyl phosphate, isopropylated triphenyl phosphate, and the like.

Di- or polyfunctional aromatic phosphorus-containing compounds are also useful, for example, compounds of the formulas below:

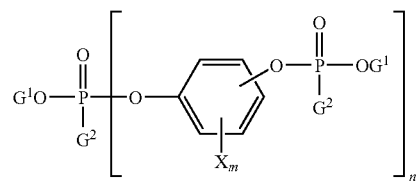

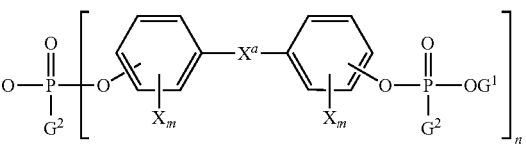

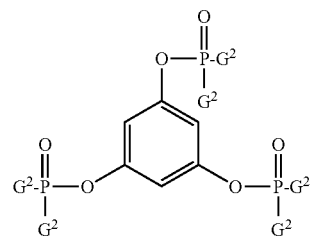

wherein each $G^1$ is independently a hydrocarbon having 1 to about 30 carbon atoms; each $G^2$ is independently a hydrocarbon or hydrocarbonoxy having 1 to about 30 carbon atoms; each X is independently a bromine or chlorine; m is 0 to 4, and n is 1 to about 30. Exemplary di- or polyfunctional aromatic phosphorus-containing compounds include resorcinol tetraphenyl diphosphate (RDP), the bis(diphenyl)phosphate of hydroquinone and the bis(diphenyl)phosphate of bisphenol-A, respectively, their oligomeric and polymeric counterparts, and the like.

Exemplary flame retardant compounds containing phosphorus-nitrogen bonds include phosphonitrilic chloride, phosphorus ester amides, phosphoric acid amides, phosphonic acid amides, phosphinic acid amides, tris(aziridinyl)phosphine oxide. When present, phosphorus-containing flame retardants are generally present in amounts of about 0.1 to about 30 parts by weight, more specifically about 1 to about 20 parts by weight, based on 100 parts by weight of silylated polycarbonate and impact modifier.

Halogenated materials can also be used as flame retardants, for example halogenated compounds and resins of formula (18):

(18)

wherein R is an alkylene, alkylidene or cycloaliphatic linkage, e.g., methylene, ethylene, propylene, isopropylene, isopropylidene, butylene, isobutylene, amylene, cyclohexylene, cyclopentylidene, or the like; or an oxygen ether, carbonyl, amine, or a sulfur containing linkage, e.g., sulfide, sulfoxide, sulfone, or the like. R can also consist of two or more alkylene or alkylidene linkages connected by such groups as aromatic, amino, ether, carbonyl, sulfide, sulfoxide, sulfone, or the like.

Ar and Ar' in formula (18) are each independently mono- or polycarbocyclic aromatic groups such as phenylene, biphenylene, terphenylene, naphthylene, or the like.

Y is an organic, inorganic, or organometallic radical, for example (1a) halogen, e.g., chlorine, bromine, iodine, fluorine or (2) ether groups of the general formula OB, wherein B is a monovalent hydrocarbon group similar to X or (3) monovalent hydrocarbon groups of the type represented by R or (4) other substituents, e.g., nitro, cyano, and the like, said substituents being essentially inert provided that there is greater than or equal to one, specifically greater than or equal to two, halogen atoms per aryl nucleus.

When present, each X is independently a monovalent hydrocarbon group, for example an alkyl group such as methyl, ethyl, propyl, isopropyl, butyl, decyl, or the like; an aryl groups such as phenyl, naphthyl, biphenyl, xylyl, tolyl, or the like; and aralkyl group such as benzyl, ethylphenyl, or the like; a cycloaliphatic group such as cyclopentyl, cyclohexyl, or the like. The monovalent hydrocarbon group can itself contain inert substituents.

Each d is independently 1 to a maximum equivalent to the number of replaceable hydrogens substituted on the aromatic rings comprising Ar or Ar'. Each e is independently 0 to a maximum equivalent to the number of replaceable hydrogens on R. Each a, b, and c is independently a whole number, including 0. When b is not 0, neither a nor c can be 0. Otherwise either a or c, but not both, can be 0. Where b is 0, the aromatic groups are joined by a direct carbon-carbon bond.

The hydroxyl and Y substituents on the aromatic groups, Ar and Ar' can be varied in the ortho, meta or para positions on the aromatic rings and the groups can be in any possible geometric relationship with respect to one another.

Included within the scope of the above formula are bisphenols of which the following are representative: 2,2-bis-(3,5-dichlorophenyl)-propane; bis-(2-chlorophenyl)-methane; bis (2,6-dibromophenyl)-methane; 1,1-bis-(4-iodophenyl)-ethane; 1,2-bis-(2,6-dichlorophenyl)-ethane; 1,1-bis-(2-chloro-4-iodophenyl)ethane; 1,1-bis-(2-chloro-4-methylphenyl)-ethane; 1,1-bis-(3,5-dichlorophenyl)-ethane; 2,2-bis-(3-phenyl-4-bromophenyl)-ethane; 2,6-bis-(4,6-dichloronaphthyl)-propane; 2,2-bis-(2,6-dichlorophenyl)-pentane; 2,2-bis-(3,5-dibromophenyl)-hexane; bis-(4-chlorophenyl)-phenyl-methane; bis-(3,5-dichlorophenyl)-cyclohexylmethane; bis-(3-nitro-4-bromophenyl)-methane; bis-(4-hydroxy-2,6-dichloro-3-methoxyphenyl)-methane; and 2,2-bis-(3,5-dichloro-4-hydroxyphenyl)-propane 2,2bis-(3-bromo-4-hydroxyphenyl)-propane. Also included within the above structural formula are: 1,3-dichlorobenzene, 1,4-dibromobenzene, 1,3-dichloro-4-hydroxybenzene, and biphenyls such as 2,2'-dichlorobiphenyl, polybrominated 1,4-diphenoxybenzene, 2,4'-dibromobiphenyl, and 2,4'-dichlorobiphenyl as well as decabromo diphenyl oxide, and the like.

Also useful are oligomeric and polymeric halogenated aromatic compounds, such as a copolycarbonate of bisphenol A and tetrabromobisphenol A and a carbonate precursor, e.g., phosgene. Metal synergists, e.g., antimony oxide, can also be used with the flame retardant. When present, halogen containing flame retardants are generally present in amounts of about 1 to about 25 parts by weight, more specifically about 2 to about 20 parts by weight, based on 100 parts by weight of silylated polycarbonate and impact modifier.

Alternatively, the thermoplastic composition can be essentially free of chlorine and bromine. Essentially free of chlorine and bromine as used herein refers to materials produced without the intentional addition of chlorine or bromine or chlorine or bromine containing materials. It is understood however that in facilities that process multiple products a certain amount of cross contamination can occur resulting in bromine and/or chlorine levels typically on the parts per million by weight scale. With this understanding it can be readily appreciated that essentially free of bromine and chlorine can be defined as having a bromine and/or chlorine content of less than or equal to about 100 parts per million by weight (ppm), less than or equal to about 75 ppm, or less than or equal to about 50 ppm. When this definition is applied to the fire retardant it is based on the total weight of the fire retardant. When this definition is applied to the thermoplastic composition it is based on the total weight of the composition, excluding any filler.

Inorganic flame retardants can also be used, for example salts of $C_{1-16}$ alkyl sulfonate salts such as potassium perfluorobutane sulfonate (Rimar salt), potassium perfluoroctane sulfonate, tetraethylammonium perfluorohexane sulfonate, and potassium diphenylsulfone sulfonate, and the like; salts formed by reacting for example an alkali metal or alkaline earth metal (for example lithium, sodium, potassium, magnesium, calcium and barium salts) and an inorganic acid complex salt, for example, an oxo-anion, such as alkali metal and alkaline-earth metal salts of carbonic acid, such as $Na_2CO_3$, $K_2CO_3$, $MgCO_3$, $CaCO_3$, and $BaCO_3$ or fluoro-anion complex such as $Li_3AlF_6$, $BaSiF_6$, $KBF_4$, $K_3AlF_6$, $KAlF_4$, $K_2SiF_6$, and/or $Na_3AlF_6$ or the like. When present, inorganic flame retardant salts are generally present in amounts of about 0.01 to about 10 parts by weight, more specifically about 0.02 to about 1 parts by weight, based on 100 parts by weight of silylated polycarbonate and impact modifier.

Anti-drip agents can also be used in the composition, for example a fibril forming or non-fibril forming fluoropolymer such as polytetrafluoroethylene (PTFE). The anti-drip agent can be encapsulated by a rigid copolymer as described above, for example styrene-acrylonitrile copolymer (SAN). PTFE encapsulated in SAN is known as TSAN. Encapsulated fluoropolymers can be made by polymerizing the encapsulating polymer in the presence of the fluoropolymer, for example an aqueous dispersion. TSAN can provide significant advantages over PTFE, in that TSAN can be more readily dispersed in the composition. An exemplary TSAN can comprise about 50 wt % PTFE and about 50 wt % SAN, based on the total weight of the encapsulated fluoropolymer. The SAN can comprise, for example, about 75 wt % styrene and about 25 wt % acrylonitrile based on the total weight of the copolymer. Alternatively, the fluoropolymer can be pre-blended in some manner with a second polymer, such as for, example, an aromatic polycarbonate resin or SAN to form an agglomerated material for use as an anti-drip agent. Either method can be used to produce an encapsulated fluoropolymer. Antidrip agents are generally used in amounts of 0.1 to 10 percent by weight, based on 100 percent by weight of silylated polycarbonate and impact modifier.

Radiation stabilizers can also be present, specifically gamma-radiation stabilizers. Exemplary gamma-radiation stabilizers include alkylene polyols such as ethylene glycol, propylene glycol, 1,3-propanediol, 1,2-butanediol, 1,4-butanediol, meso-2,3-butanediol, 1,2-pentanediol, 2,3-pentanediol, 1,4-pentanediol, 1,4-hexandiol, and the like; cycloalkylene polyols such as 1,2-cyclopentanediol, 1,2-cyclohexanediol, and the like; branched alkylenepolyols such as 2,3-dimethyl-2,3-butanediol(pinacol), and the like, as well as alkoxy-substituted cyclic or acyclic alkanes. Unsaturated alkenols are also useful, examples of which include 4-methyl-4-penten-2-ol, 3-methyl-pentene-3-ol, 2-methyl-4-penten-2-ol, 2,4-dimethyl-4-pene-2-ol, and 9-decen-1-ol, as well as tertiary alcohols that have at least one hydroxy substituted tertiary carbon, for example 2-methyl-2,4-pentanediol(hexylene glycol), 2-phenyl-2-butanol, 3-hydroxy-3-methyl-2-butanone, 2-phenyl-2-butanol, and the like, and cyclic tertiary alcohols such as 1-hydroxy-1-methyl-cyclohexane. Certain hydroxymethyl aromatic compounds that have hydroxy substitution on a saturated carbon attached to an unsaturated carbon in an aromatic ring can also be used. The hydroxy-substituted saturated carbon can be a methylol group (—$CH_2OH$) or it can be a member of a more complex hydrocarbon group such as —$CR^4HOH$ or —$CR_2^4OH$ wherein $R^4$ is a complex or a simple hydrocarbon. Specific hydroxy methyl aromatic compounds include benzhydrol, 1,3-benzenedimethanol, benzyl alcohol, 4-benzyloxy benzyl alcohol and benzyl benzyl alcohol. 2-Methyl-2,4-pentanediol, polyethylene glycol, and polypropylene glycol are often used for gamma-radiation stabilization. Gamma-radiation stabilizing compounds are typically used in amounts of 0.05 to 1 parts by weight based on 100 parts by weight of silylated polycarbonate and impact modifier.

The thermoplastic composition comprising the silylated polycarbonate can further have other desirable properties. In an embodiment, an article having a thickness of 3.2 mm and molded from the thermoplastic composition has a NII strength of 20 to 100 Joules per meter (J/m), measured at 23° C. in accordance with ASTM D256-04. In another embodiment, an article having a thickness of 3.2 mm and molded from the thermoplastic composition has a haze of less than 10%, measured in accordance with ASTM D1003-00. In another embodiment, an article having a thickness of 3.2 mm and molded from the thermoplastic composition has a Dynatup Ductility total energy of 4 to 40 Joules as measured by ASTM D3763-02.

Thermoplastic compositions comprising the silylated polycarbonate can be manufactured by various methods. For example, powdered silylated polycarbonate, other polymer (if present), and/or other optional components are first blended, optionally with fillers in a HENSCHEL-Mixer® high speed mixer. Other low shear processes, including but not limited to hand mixing, can also accomplish this blending. The blend is then fed into the throat of a twin-screw extruder via a hopper. Alternatively, at least one of the components can be incorporated into the composition by feeding directly into the extruder at the throat and/or downstream through a sidestuffer. Additives can also be compounded into a masterbatch with a desired polymeric resin and fed into the extruder. The extruder is generally operated at a temperature higher than that necessary to cause the composition to flow. The extrudate is immediately quenched in a water batch and pelletized. The pellets, so prepared, when cutting the extrudate can be one-fourth inch long or less as desired. Such pellets can be used for subsequent molding, shaping, or forming.

Shaped, formed, or molded articles comprising the silylated polycarbonate compositions are also provided. The polycarbonate compositions can be molded into useful shaped articles by a variety of means such as injection molding, extrusion, rotational molding, blow molding and thermoforming to form articles such as, for example, automotive components such as side panels, deck lids, bumpers, lenses for head lamps, bottles, and containers (e.g., for medical applications); transparent parts in consumer electronics, such as mobile phones, PDAs, mp3 players, and the like.

The silylated polycarbonates are further illustrated by the following non-limiting examples.

High performance Liquid Chromatography (HPLC) was used to check the purity of bisphenol siloxane products prepared in the following examples. An Xterra C18 column having dimension 4.6 mm×50 mm and particle size 5 micrometers was used for the analysis. The column temperature was maintained at 30° C. The column was eluted with a water-acetonitrile eluent system having 40 percent water and 60 percent acetonitrile in a volume to volume (v/v) ratio. The flow rate of the eluent was 1.00 ml per minute. The sample solution was prepared by dissolving the 20 milligram (mg) of the bisphenol siloxane product in 10 ml of acetonitrile. 5 microliters (µl) of the sample solution was injected in the column and the sample was eluted over a total run time of 41 minutes.

Proton NMR spectra for all bisphenol siloxane compounds and 2,2'-diallylbisphenol A described herein were measured using a 300 megahertz (MHz) Bruker NMR spectrometer using deuterated chloroform ($CDCl_3$) as the solvent. Proton NMR spectra for 4,4'-diallyloxydiphenyl and 3,3'-diallylbiphenyl-4,4'-diol described herein were measured using a 300 megahertz Bruker NMR spectrometer using deuterated dimethylsiloxane (DMSO-$d_6$) as the solvent. The samples for the analysis was prepared by dissolving about 5 to 7 milligrams (mg) of the sample in 0.75 milliliter (ml) of NMR solvent.

An Agilent 6890 series gas chromatograph (GC) coupled with a 5973N MS detector was used to record the gas chromatography-mass spectrograph (GCMS) for the bisphenol siloxane products. The Hewlett-Packard Ultra-2 capillary column having a dimension of length 50 meter (m) and diameter 0.320 millimeter (mm) and a film thickness of 0.52 micrometer was used. Helium gas at a flow rate of 1.2 ml per minute was used to elute the sample in the column. The sample for injection was prepared by dissolving bisphenol siloxane (2 mg) in 1 ml of acetonitrile. 1 microliter of the sample was injected in the column at an injection temperature of 320° C. The oven temperature was increased from 80° C. to 300° C. at a rate of 15° C. per minute and held at 300° C. for 15 minutes.

Monomer Example 1

Preparation of bisphenol A-siloxane monomer

Step A. Purification of commercially available 2,2'-diallylbisphenol A. To a 250 ml three neck round-bottomed flask maintained at 25° C. and equipped with a water condenser was added 2,2'-diallylbisphenol A (40 grams (g)) and an aqueous solution of sodium hydroxide (130 milliliters (ml), as a 12 percent weight to volume (w/v) solution of sodium hydroxide in water). The resultant mixture was heated to 65° C. After stirring at 65° C. for 1 hour the mixture was cooled to 25° C. Toluene (100 ml) was added and the resultant mixture stirred for about 0.5 hours. The resultant mixture when allowed to stand for about 10 minutes separated into an aqueous layer and an organic (toluene) layer. The aqueous layer was separated, treated with toluene (100 ml) and the resultant mixture when allowed to stand for about 10 minutes separated into an aqueous layer and an organic (toluene) layer. To the resultant aqueous layer was added hydrochloric acid (2.75 Normality; 160 ml). The resultant mixture was then treated with toluene (3×150 ml) in the same manner as above. The separated organic (toluene) layer was dried over anhydrous sodium sulfate and toluene distilled out from the organic layer to provide 35.7 g of purified 2,2'-diallylbisphenol A.

Proton NMR spectrum of the purified 2,2'-diallylbisphenol A showed peaks at δ 1.6 (s, 6H, —C(CH$_3$)$_2$), 3.4 (d, 4H, ArCH$_2$), 4.9 (br, 2H, —OH), 5.1 (m, 4H, allyl CH$_2$), 6.0 (m, 2H, allyl CH), 6.7 (m, 2H, Ar), and 7.0 (m, 4H, Ar).

Step B. Preparation of bisphenol A-siloxane. To a 1 L three neck round-bottomed flask maintained at 25° C. and under nitrogen atmosphere was added heptamethyltrisiloxane (52.1 g) and toluene (40 ml). The resultant mixture was heated to 40° C. To the solution maintained at 40° C. and under nitrogen atmosphere was added a solution of 2,2'-diallyl bisphenol A (35.7 g, from Step A) and Karstedt's catalyst (40 mg) (Platinum-divinyl tetramethyl-disiloxane complex in vinylsilicone, 3.0-3.5 pt concentration in vinyl terminated PDMSO) in toluene (80 ml) prepared separately in another flask. The temperature of the reaction mixture was then raised to about 60° C. to 65° C. and the mixture was stirred at 60° C. to 65° C. for 7 hours. The temperature was then decreased to 25° C., the mixture filtered through a silica bed (60 to 120 mesh), and toluene distilled off from the filtrate to provide 77.8 g bisphenol A-siloxane as an oily liquid.

Step C. Purification of bisphenol A-siloxane prepared in Step B. Bisphenol A-siloxane (77.8 g) as prepared in Step B was dissolved in hexane (250 ml) to form a solution. To the solution was added silica gel (60 to 120 mesh; 8.0 g). The resultant mixture was stirred at 25° C. for about 30 minutes. Activated charcoal (3.0 g) was added to the mixture and the resultant mixture was stirred at 25° C. for about 2 hours. The mixture was then filtered through a Celite® bed. Hexane was distilled out from the filtrate to provide 68.4 g of bisphenol A-siloxane.

Proton NMR spectrum of the bisphenol A-siloxane showed peaks at δ 0.1 (m, 42H, —SiCH$_3$), 0.5 (t, 4H, —SiCH$_2$), 1.6 (m, 10H, C(CH$_3$)$_2$ and CCH$_2$C), 2.6 (t, 4H, benzyl CH$_2$), 4.8 (br, 2H, —OH), 6.7 (m, 2H, Ar), 7.0 (m, 4H, Ar).

Mass spectral analysis of the product of Monomer Example (1a) indicates peaks corresponding to the presence of a monomer having a structure corresponding to that of formula (1a), in addition to several other isomers and by-products resulting from the hydrosilylation reaction, as shown in Table 1.

TABLE 1

| Isomer Number | Isomer Structure | m/z (g/mol) | mol % of Composition (Monomer Ex. 1) |
|---|---|---|---|
| 1 | [structure] | 752 | 85 |
| 2 | [structure] | 752 | 5 |
| 3 | [structure] | 750 | 2.7 |

TABLE 1-continued

| Isomer Number | Isomer Structure | m/z (g/mol) | mol % of Composition (Monomer Ex. 1) |
|---|---|---|---|
| 4 | [structure with siloxane group, biphenol with allyl substituent] | 530 | 0.8 |
| 5 | [structure with siloxane group, biphenol with propyl substituent] | 532 | 2.5 |
| 6 | [structure with siloxane group, biphenol] | 490 | 1.3 |
| 7 | Other bisphenols | — | 2.7 |

Monomer Example 2

Preparation of biphenol-siloxane

Step A. Preparation of 4,4'-diallyloxydiphenyl. To a 500 ml three neck round-bottomed flask maintained at 25° C., maintained under nitrogen atmosphere and equipped with a water condenser were added 4,4'-dihydroxydiphenyl (38.3 g), absolute ethanol (300 ml), potassium carbonate (57.9 g) and potassium iodide (6.15 g). The resultant mixture was stirred for about 10 minutes. Allyl chloride (87 ml) is added to the flask at a rate of 10 ml per minute. The resultant mixture was then heated to 89° C. After being refluxed at 89° C. for about 20 hours the mixture was cooled to 25° C. The resultant solid was filtered, washed with water (500 ml) and dried at 60° C. to provide 46.5 g of the desired product.

Proton NMR spectrum of the 4,4'-diallyloxydiphenyl showed peaks at δ 4.6 (d, 4H, O—CH$_2$), 5.3-5.4 (m, 4H, allyl CH$_2$), 6.1 (m, 2H, allyl CH), 7.0 (d, 4H, Ar, ortho to O-allyl), and 7.6 (d, 4H, Ar, meta to O-allyl).

Step B. Preparation of 3,3'-diallylbiphenyl-4,4'-diol. (See Britton et. al., U.S. Pat. No. 2,229,010). To a 100 ml three neck round-bottomed flask maintained under nitrogen atmosphere was charged 4,4'-diallyloxydiphenyl (36 g) and diethylaniline (36 ml). The resultant mixture was heated to a temperature of 240° C. to 244° C. in a period of 30 minutes. After maintaining the mixture at 240° C. to 244° C. for a period of 30 minutes under nitrogen atmosphere the mixture was cooled to 25° C. Sodium hydroxide solution (360 ml, as a 7.5 percent w/v solution of sodium hydroxide in water) was added to the mixture and the resultant mixture was stirred for about 20 minutes. Toluene (250 ml) was added to the mixture under stirring. The resultant mixture on standing for about 10 minutes separated into an aqueous layer and an organic (toluene layer). The aqueous layer was separated and treated twice with toluene (250 ml) in the same manner as described above. To the resultant aqueous layer was added sulfuric acid (270 ml, mixture of 27 ml 98 percent sulfuric acid and 243 ml water). On addition of sulfuric acid solids separated out from the resultant mixture. The mixture was then cooled to 10° C. After stirring at 10° C. for about 20 minutes the solid was filtered off, washed with water (5×100 ml) and dried at 60° C. for 4 hours. The resultant dry solid was dissolved in toluene (180 ml) at 25° C. To the resultant solution was added petroleum ether (180 ml) and the resultant solution was cooled to 10° C. After stirring at 10° C. for about 30 minutes the solid that separated out was filtered and dried at 60° C. for 5 hours to give 22.3 g of the recrystallized product. The product had a melting point of 80° C.

Proton NMR spectrum of the 3,3'-diallylbiphenyl-4,4'-diol showed peaks at δ 3.3 (m, 4H, ArCH$_2$), 5.0 (m, 4H, allyl CH$_2$), 6.0 (m, 2H, allyl CH), 6.8 (d, 2H, Ar), 7.2 (m, 4H, Ar), and 9.3 (br, 2H, —OH).

Step C. Preparation of biphenol-siloxane. To a 1 L three neck round-bottomed flask maintained at 25° C. and under nitrogen atmosphere were added 3,3'-diallylbiphenyl-4,4'-diol (22.3 g), heptamethyltrisiloxane (38.1 g), toluene (100 ml) and Karstedt's catalyst (26.7 mg). The resultant mixture was heated to 100° C. The mixture was maintained at 100° C. for about 28 hours. The resultant mixture was filtered through silica gel (60 to 120 mesh). Toluene was distilled out from the filtrate to provide 58 g of the desired product in the form of oil. The crude material was purified by column chromatography. Silica gel (60 to 120 mesh) was used as the column packing and ethyl acetate:hexane in a ratio of 0:100 to 10:90 volume to volume was used as the eluent. The desired product was obtained in a yield of about 12 g of in the form of oil and a purity of 96.4 percent as determined by HPLC.

Proton NMR spectrum of the biphenol-siloxane showed peaks at δ 0.2 (m, 42H, Si—CH$_3$), 0.6 (m, 4H, SiCH$_2$), 1.8 (m, 4H, —C—CH$_2$—C—), 2.7 (m, 4H, benzyl CH$_2$), 5.0 (br, 2H, —OH), 6.8 (d 2H, Ar), 7.3 (m, 4H, Ar).

Polymer Examples 1-4

Polymer Examples 1-4 comprising structural units derived from bisphenol A-siloxane (from Monomer Example 1) and bisphenol A were prepared using bismethylsalicylcarbonate in a process for preparing the copolymer. The amounts of the reactants used are included in Table 2, below.

To a cylindrical polymerization reactor made of glass and having a length of 29 cm, outer diameter 3.8 cm and inner diameter 3.2 cm, were charged bisphenol A, bismethylsalicylcarbonate, and bisphenol A-siloxane to form a reactant mixture. 400 microliters (µl) of a solution containing tetramethylammonium hydroxide (2.6 mg) and sodium hydroxide (9.58 mg) was added to the reaction mixture. The reactor was subjected to a vacuum of less than one millibar and then subsequently purged with nitrogen. This process of subjecting the reactor to vacuum followed by purging with nitrogen gas was repeated three times. Finally the pressure inside the reactor was raised to atmospheric pressure by nitrogen. The reactor was then heated to 180° C. in a period of about 15 minutes to provide a molten mixture of the contents. After holding at 180° C. and atmospheric pressure for about 5 minutes and after beginning stirring, the temperature was raised to 190° C. After stirring the mixture at 190° C. for 15 minutes, the temperature was increased to 210° C. under atmospheric pressure over about 5 minutes. After holding at 210° C. and atmospheric pressure for about 5 minutes, and further increasing the temperature to and holding at 220° C. for another 5 minutes, the temperature was further increased to 230° C. over about 5 minutes and the pressure was reduced to 100 millibar in about 10 minutes. After holding at 230° C. and 100 millibar for about 10 minutes and further increasing the temperature to and holding at 240° C. and 100 millibar for another 10 minutes, the temperature of the reactor was raised to 260° C. in about 5 minutes and the pressure was simultaneously reduced to less than one millibar. After holding at 260° C. and less than one millibar for about 10 minutes and then increasing the temperature to and holding at 275° C. and less than one millibar for another 5 minutes, the pressure inside the reactor was raised to atmospheric pressure and the desired copolymer was isolated in a yield of about 20 grams. Data for the copolymer samples prepared by this method are provided in Table 2 below.

Polymer Examples 5-7

Polymer Examples 5-7 comprising structural units derived from bisphenol A-siloxane (from Monomer Example 1) and bisphenol A were prepared using triphosgene in a process for preparing the copolymer. The amounts of the reactants used is included in Table 2, below.

To a 4 necked round-bottomed flask fitted with two dropping funnels and a mechanical stirrer and maintained under nitrogen atmosphere were charged bisphenol A, bisphenol A-siloxane, water (100 ml), dichloromethane (100 ml) and triethylbenzylammonium chloride (0.2 grams) to form a mixture. The flask was maintained at a temperature of 25° C. under nitrogen atmosphere. The mixture was stirred at a stirrer speed of 700 rpm. To the resultant mixture was added triphosgene (TP) as a solution in dichloromethane (50 ml) in a drop-wise manner thought one of the dropping funnels in a period of about 15 to 20 minutes. The pH of the resultant mixture was maintained at about 5 to 6 by simultaneously adding required quantity of aqueous sodium hydroxide solution (30 percent w/v sodium hydroxide in water) through the second dropping funnel. After stirring the resultant mixture for another 30 minutes the pH of the mixture was raised to about 10 to 11 by adding the required amount of aqueous sodium hydroxide solution as described above. To the resultant mixture were added triethylamine (150 µl), dichloromethane (5 ml) and p-cumyl phenol (318 mg). The pH of the resultant mixture was increased to about 12 by adding the required amount of aqueous sodium hydroxide solution as described above. After stirring the mixture for 10 minutes the reaction was diluted with further 15 ml of dichloromethane and 50 ml of water and was allowed to stand for about 15 minutes, by which time the mixture separated into an aqueous layer and an organic dichloromethane layer. The organic dichloromethane layer was separated and washed with dilute hydrochloric acid (1N) (3×100 ml). The acid washed organic dichloromethane layer was then washed with water (3×500 ml), dried over anhydrous sodium sulfate. The organic dichloromethane layer was added to 300 ml methanol under stirring, the resultant precipitated polymer filtered from the mixture, and the filter cake air dried to provide the desired product in a yield of 30 grams. Data for the copolymer samples prepared by this method is provided in Table 2 below.

Polymer Example 8-10

Polymer Examples 8-10 comprising structural units derived from bisphenol A-siloxane (from Monomer Example 1) and bisphenol A were prepared using diphenylcarbonate in a process for preparing the copolymer. The amounts of the reactants used are included in Table 2, below.

To a cylindrical polymerization reactor made of glass and having a length of 29 cm, outer diameter 3.8 cm and inner diameter 3.2 cm, were charged bisphenol A, diphenyl carbonate (DPC), and bisphenol A-siloxane to form a reactant mixture. 400 µl of a solution containing tetramethylammonium hydroxide (2.6 mg) and sodium hydroxide (9.58 mg) was added to the reaction mixture. The reactor was subjected to a vacuum of less than one millibar and then subsequently purged with nitrogen. This process of subjecting the reactor to vacuum followed by purging with nitrogen gas was repeated three times. Finally the pressure inside the reactor was raised to atmospheric pressure by nitrogen. The reactor was then heated to 150° C. in a period of about 15 minutes to provide a molten mixture of the contents. After holding at 150° C. and atmospheric pressure for about 5 minutes, stirring was started. After stirring the mixture at 150° C. for 15 minutes, the temperature was increased to 220° C. under atmospheric pressure in a period of about 5 minutes. After holding at 220° C. and atmospheric pressure for another 60 minutes, the temperature was increased to 230° C. in about 5 minutes and the pressure was simultaneously reduced to 170 millibar. After holding at 230° C. and 170 millibar for about 30 minutes and, increasing the temperature to and holding at 240° C. and 170 millibar for another 30 min, the temperature of the reactor was raised to 260° C. in about 5 minutes and the pressure was simultaneously reduced to 20 millibar. After holding at 260° C. and 20 millibar for about 10 minutes and then increasing the temperature to and holding at 270° C. and 20 millibar for another 20 min, the temperature was increased to 280° C. in about 5 minutes and the pressure was simultaneously reduced to less than one millibar. After holding at 280° C. and less than one millibar for about 60 minutes, the pressure inside the reactor was raised to atmospheric pressure and the desired copolymer was isolated in a yield of about 30 grams. Data for the copolymer samples prepared by this method is provided in Table 2, below.

TABLE 2

| Polymer Example | Carbonating agent | Amount of carbonating agent (g) | Mol % bisphenol A-siloxane | Bisphenol A (g) | Bisphenol A-siloxane (g) | Mw[a] | Mn[a] | PDI[a] | Molar Ratio of (Bisphenol A to Bisphenol A-siloxane) to carbonating agent | Tg (° C.)[a] |
|---|---|---|---|---|---|---|---|---|---|---|
| 1 | BMSC | 30 | 3.3 | 19.67 | 2.09 | — | | | 1.030 | — |
| 2 | BMSC | 30 | 3.3 | 19.86 | 2.11 | 86700 | 44400 | 1.95 | 1.020 | 126[b] |
| 3 | BMSC | 30 | 15.5 | 17.36 | 9.91 | — | | | 1.020 | — |
| 4 | BMSC | 30 | 15.5 | 17.44 | 9.96 | 84100 | 24594 | 3.42 | 1.015 | 85 |
| 5 | Triphosgene | 15.20 | 3.3 | 22.08 | 2.34 | 36100 | 18300 | 1.97 | Ratio of equivalents of triphosgene to (BPA and Bisphenol A-siloxane) is 1:1; PCP end-cap = 3 mol % | 124 |
| 6 | Triphosgene | 15.20 | 3.3 | 22.08 | 2.34 | 43409 | 19350 | 2.24 | Ratio of equivalents of triphosgene to (BPA and Bisphenol A-siloxane) is 1:1; PCP end-cap = 2 mol % | 126 |
| 7 | Triphosgene | 15.20 | 3.3 | 22.08 | 2.34 | 191706 | 88279 | 2.17 | Ratio of equivalents of triphosgene to (BPA and Bisphenol A-siloxane) is 1:1; PCP end-cap = 1 mol % | 130 |
| 8 | DPC | 30 | 3.3 | 30.014 | 3.187 | — | | | 1.050 | — |
| 9 | DPC | 30 | 3.3 | 30.3 | 3.22 | 21500 | 11000 | 1.95 | 1.040 | 128 |
| 10 | DPC | 30 | 3.3 | 30.6 | 3.25 | 30300 | 15500 | 1.95 | 1.030 | 128 |

[a]Not done for Polymer Examples 1, 3 and Comp. Ex. 8 because of excessively low Mw and Mn
[b]Tg of 3.3 mol % coPC varies between 124 and 130° C. depending on Mw, Mn.

For the carbonate sources DPC and BMSC, the theoretical mole ratio requirement of total carbonate to total phenol for a particular range of molecular weight should not vary with comonomer concentration distributions. However, the bisphenol A-siloxane monomer contained about 15 wt % impurities (including other isomers and reaction by-products), which when converted to mol % on the basis of HPLC peak integral values and proposed molecular structures (see Table 1) can be responsible for some minimal error in actual stoichiometry for the monomers. For copolymers prepared using higher amounts (i.e., 15.5 mol % of bisphenol A-siloxane based on the total monomer loading, as seen in Polymer Examples 3 and 4), accounting for the impurities and/or isomers is necessary to provide greater accuracy in the stoichiometry of bisphenol A-siloxane to bisphenol A in the polymer examples, more so than was needed where the total bisphenol A-siloxane loading is 3.3 mol % (Polymer Examples 1, 2, and 5-10) based on the total monomer loading.

It is noted as well that, for the triphosgene mediated interfacial polymerization, molecular weight control has been found to be governed by the para-cumyl phenol (PCP) endcapping agent concentration and not the mole ratio of phenol and triphosgene (i.e., the carbonate source in Polymer Examples 5-7), and hence, the ratio of concentrations of phenol and triphosgene is constant for these copolymerizations.

Preparation and Evaluation of thermoplastic compositions. Thermoplastic compositions (Examples 1 and 2, and Comparative Examples 1-3) were prepared using the silylated polycarbonate of Polymer Examples 2 and 4, and components listed in Table 3, below.

TABLE 3

| Name | Description | Manufacturer |
|---|---|---|
| PC 105 | Bisphenol A polycarbonate, 105 grade | GE Plastics |
| PC 175 | Bisphenol A polycarbonate, 175 grade | GE Plastics |
| PC/PDMS | PC/PDMS copolymer, (20 wt % siloxane content) | GE Plastics |
| MZP | Mono zinc phosphate | — |
| I-168 | Tris(2,6-di-tert-butylphenyl)phosphite) (Antioxidant) | Ciba Specialty Chemicals |

Examples 1 and 2 and Comparative Examples 1-4 were formulated as described in Table 4, below and mixed in a Henschel™ tumbler for 5 to 10 minutes. Then, the formulations were extruded on a Wayne single screw extruder and pelletized. The pellets were injection molded into 3.2 mm thick parts for analysis.

TABLE 4

| Component | Ex. 1 (wt %) | Ex. 2 (wt %) | CEx. 1 (wt %) | CEx. 2 (wt %) | CEx. 3 (wt %) | CEx. 4 (wt %) |
|---|---|---|---|---|---|---|
| Polymer Example 2 | 100 | — | — | — | — | — |
| Polymer Example 4 | — | 100 | — | — | — | — |
| PC 175 | — | — | — | — | 45 | — |
| PC 105 | — | — | 100 | 77.71 | 37.45 | — |
| PC/PDMS | — | — | — | 22.2 | 17.5 | 100 |
| MZP | — | — | — | — | 0.05 | — |
| I-168 | — | — | — | 0.09 | — | — |

Surface contact angle measurements of Examples 1 and 2 and Comparative Examples 1-3. Surface contact angle measurements were performed using a Krüss Drop Shape Analysis System DSA10, depositing Milli-Q® purified water (as purified using the purification system obtained from Millipore Corp.) as a fluid test probe to form the sessile drop. As shown in FIG. 1, using the sessile drop method, a drop of water is deposited on the surface or substrate to be tested, and the contact angle (θ) between the surface and the 3 phase tangent line emanating from a point at the junction of the three phases, i.e., the surface, the water drop, and the air, is measured by the system automatically. In performing the measurement, the system deposits a 15 ml drop of water onto specimen surface. From a live video image captured, the system automatically measures the contact angle as the angle between the substrate and the tangent of the water drop surface at the 3-phase contact line that the water drop makes with the surface of the specimen. The results are as shown in Table 5.

TABLE 5

| Contact Angle (°) | CEx. 1 | CEx. 2 | CEx. 3 | Ex. 1 | Ex. 2 |
|---|---|---|---|---|---|
| max | 81.7 | 98.9 | 98.4 | 86 | 102 |
| mean | 81.3 | 96.7 | 96.9 | 83-84 | 100.1 |
| min | 80.9 | 95.2 | 96.1 | 81 | 97.6 |

Figure 2:
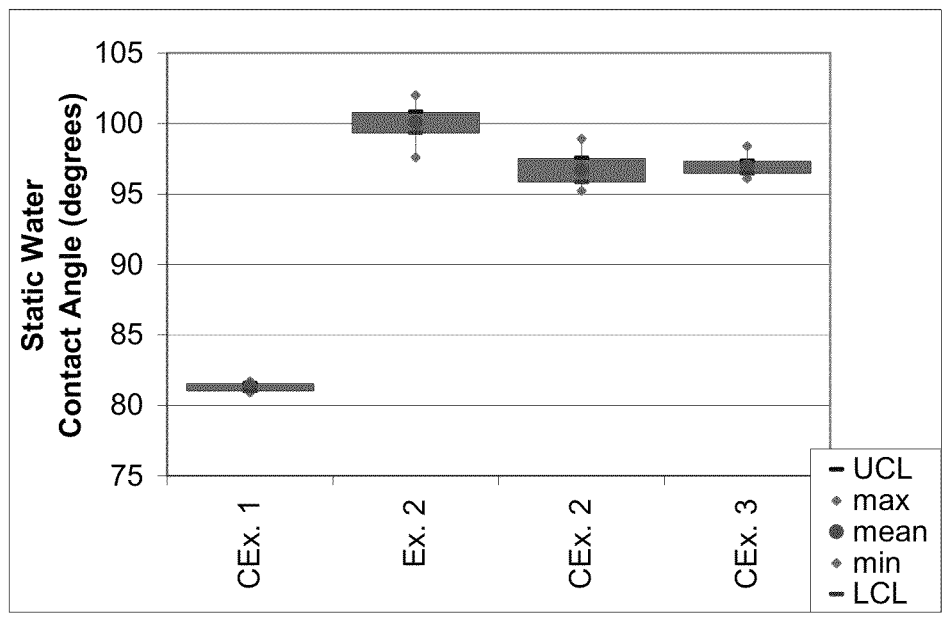
FIG. 2 is a plot of contact angle for Example 2 and Comparative Examples 1-3.

From the results shown in Table 5, it can be seen that the contact angle for Example 1, having 3.3 mol % bisphenol siloxane monomer (Monomer Example 1) is higher in mean contact angle than Comparative Example 1 and lower in contact angle than that measured for Comparative Examples 2 and 3. Example 2, having 15.5 mol % of the bisphenol siloxane monomer and a siloxane content of about 20 wt %, has a significantly higher mean water contact angle than Comparative Example 1 (bisphenol A polycarbonate, 105 grade), and a higher mean water contact angle than either a blend of bisphenol A polycarbonate with PDMS/PC copolymer having a siloxane content of 4.4 wt % (Comparative Example 2) or than a similar blend having a siloxane content of 3.5 wt % (Comparative Example 3). The results for Example 2, and Comparative Examples 1-3, are shown graphically in FIG. 2.

The singular forms "a," "an," and "the" include plural referents unless the context clearly dictates otherwise. Unless defined otherwise, technical and scientific terms used herein have the same meaning as is commonly understood by one of skill in the art to which this invention belongs. The endpoints of all ranges directed to the same component or property are inclusive and independently combinable (e.g., ranges of "less than or equal to about 25 wt %, or, more specifically, about 5 wt % to about 20 wt %," is inclusive of the endpoints and all intermediate values of the ranges of "about 5 wt % to about 25 wt %," etc.). The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like. All references are incorporated herein by reference.

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group.

As used herein, the term "hydrocarbyl" refers broadly to a substituent comprising carbon and hydrogen, optional with at least one heteroatoms, for example, oxygen, nitrogen, halogen, or sulfur; "alkyl" refers to a straight or branched chain monovalent hydrocarbon group; "alkylene" refers to a straight or branched chain divalent hydrocarbon group; "alkylidene" refers to a straight or branched chain divalent hydrocarbon group, with both valences on a single common carbon atom; "alkenyl" refers to a straight or branched chain monovalent hydrocarbon group having at least two carbons joined by a carbon-carbon double bond; "cycloalkyl" refers to a non-aromatic monovalent monocyclic or multicylic hydrocarbon group having at least three carbon atoms, "cycloalkenyl" refers to a non-aromatic cyclic divalent hydrocarbon group having at least three carbon atoms, with at least one degree of unsaturation; "aryl" refers to an aromatic monovalent group containing only carbon in the aromatic ring or rings; "arylene" refers to an aromatic divalent group containing only carbon in the aromatic ring or rings; "alkylaryl" refers to an aryl group that has been substituted with an alkyl group as defined above, with 4-methylphenyl being an exemplary alkylaryl group; "arylalkyl" refers to an alkyl group that has been substituted with an aryl group as defined above, with benzyl being an exemplary arylalkyl group; "acyl" refers to an alkyl group as defined above with the indicated number of carbon atoms attached through a carbonyl carbon bridge (—C(=O)—); "alkoxy" refers to an alkyl group as defined above with the indicated number of carbon atoms attached through an oxygen bridge (—O—); and "aryloxy" refers to an aryl group as defined above with the indicated number of carbon atoms attached through an oxygen bridge (—O—).

While typical embodiments have been set forth for the purpose of illustration, the foregoing descriptions should not be deemed to be a limitation on the scope herein. Accordingly, various modifications, adaptations, and alternatives can occur to one skilled in the art without departing from the spirit and scope herein.

What is claimed is:

1. A silylated dihydroxy aromatic compound of formula (1a):

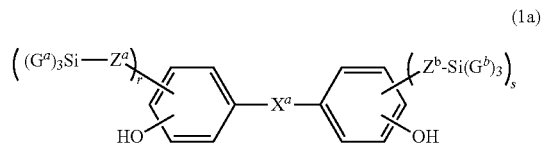

wherein:

$G^a$ and $G^b$ are each independently —OSi($C_{1-12}$ alkyl)$_3$ or —OSi($C_{7-12}$ arylalkyl)$_3$;

$Z^a$ and $Z^b$ are each independently a straight or branched $C_{2-18}$ alkylene, a $C_{8-18}$ arylalkylene, or a $C_{8-18}$ alkylarylene;

$X^a$ is a direct bond, a heteroatom-containing group, or a C1-18 organic group;

r and s are each 1.

2. A silylated dihydroxy aromatic compound of formula (1a):

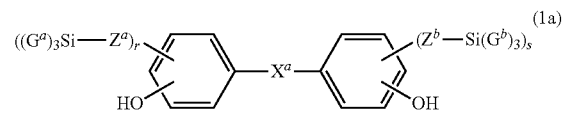

wherein:

$G^a$ and $G^b$ are each independently $C_{1-12}$ alkyl, —OSi($C_{1-12}$ alkyl)$_3$, $C_{1-12}$ arylalkyl, or —OSi($C_{1-12}$ arylalkyl)$_3$;

$Z^a$ and $Z^b$ are each independently a straight or branched $C_{2-18}$ alkylene, a $C_{8-18}$ arylalkylene, or a $C_{8-18}$ alkylarylene;

$X^a$ is a direct bond, a heteroatom-containing group, or a C1-18 organic group;

r is 1 or 2; and s is 2.

3. The silylated dihydroxy aromatic compound of claim 2, wherein r is 2.

4. The silylated dihydroxy aromatic compound of claim 2, wherein $G^a$ and $G^b$ are each independently —OSi($C_{1-12}$ alkyl)$_3$.

5. The silylated dihydroxy aromatic compound of claim 2, wherein $X^a$ is a direct bond.

6. The silylated dihydroxy aromatic compound of claim 2, wherein $X^a$ has the structure of formula (3):

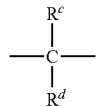

wherein:
$R^c$ and $R^d$ are each independently hydrogen or $C_{1-12}$ alkyl.

7. The silylated dihydroxy aromatic compound of claim 2, wherein $X^a$ is a heteroatom selected from —O—, —S— or —N(Z)—, where Z is hydrogen or $C_{1-12}$ alkyl.

8. A silylated polycarbonate polymer or copolymer comprising the reaction product of at least one silylated dihydroxy aromatic compound of the formula (1a):

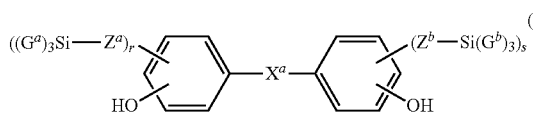

wherein:
$G^a$ and $G^b$ are each independently $C_{1-12}$ alkyl, —OSi($C_{1-12}$ alkyl)$_3$, $C_{1-12}$ arylalkyl, or —OSi($C_{1-12}$ arylalkyl)$_3$;
$Z^a$ and $Z^b$ are each independently a straight or branched $C_{2-18}$ alkylene, a $C_{8-18}$ arylalkylene, or a $C_{8-18}$ alkylarylene;
$X^a$ is a direct bond, a heteroatom-containing group, or a C1-18 organic group;
r is 1 or 2; and
s is 2.

9. The silylated polycarbonate polymer or copolymer of claim 8, wherein r is 2 in structure of the silylated dihydroxy aromatic compound.

10. The silylated polycarbonate polymer or copolymer of claim 8, wherein $G^a$ and $G^b$ are each independently —OSi($C_{1-12}$ alkyl)$_3$ in the structure of the silylated dihydroxy aromatic compound.

11. The silylated polycarbonate polymer or copolymer of claim 8, wherein $X^a$ has the structure of formula (3):

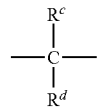

wherein:
$R^c$ and $R^d$ are each independently hydrogen or $C_{1-12}$ alkyl.

12. The silylated polycarbonate polymer or copolymer of claim 8 further comprises units derived from bisphenol having the formula (8):

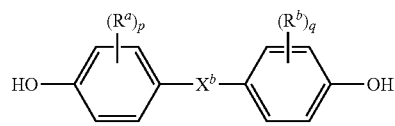

wherein:
$R^a$ and $R^b$ each are a halogen or $C_{1-12}$ alkyl;
p and q are each independently 0 to 4.

13. A silylated polycarbonate polymer or copolymer comprising the reaction product of at least one silylated dihydroxyl aromatic compound of formula (1a):

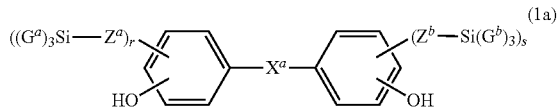

wherein:
$G^a$ and $G^b$ are each independently —OSi($C_{1-12}$ alkyl)$_3$ or —OSi($C_{7-12}$ arylalkyl)$_3$;
$Z^a$ and $Z^b$ are each independently a straight or branched $C_{2-18}$ alkylene, a $C_{8-18}$ arylalkylene, or a $C_{8-18}$ alkylarylene;
$X^a$ is a direct bond, a heteroatom-containing group, or a C1-18 organic group;
r and s are each 1.

* * * * *